(12) United States Patent
Margulies et al.

(10) Patent No.: US 11,026,945 B2
(45) Date of Patent: Jun. 8, 2021

(54) PROTEIN KINASE RNA-LIKE ENDOPLASMIC RETICULUM KINASE (PERK) INHIBITORS FOR PREVENTION AND/OR TREATMENT OF LUNG INJURY AND/OR INFLAMMATION

(71) Applicant: THE TRUSTEES OF THE UNIVERSITY OF PENNSYLVANIA, Philadelphia, PA (US)

(72) Inventors: Susan S. Margulies, Villanova, PA (US); Tamas Dolinay, Wynnewood, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 0 days.

(21) Appl. No.: 16/096,721

(22) PCT Filed: Apr. 27, 2017

(86) PCT No.: PCT/US2017/029820
§ 371 (c)(1),
(2) Date: Oct. 26, 2018

(87) PCT Pub. No.: WO2017/189837
PCT Pub. Date: Nov. 2, 2017

(65) Prior Publication Data
US 2020/0054638 A1    Feb. 20, 2020

Related U.S. Application Data

(60) Provisional application No. 62/329,955, filed on Apr. 29, 2016.

(51) Int. Cl.
| | | |
|---|---|---|
| *A61K 31/519* | (2006.01) | |
| *A61P 11/00* | (2006.01) | |
| *C12N 15/113* | (2010.01) | |

(52) U.S. Cl.
CPC .......... *A61K 31/519* (2013.01); *A61P 11/00* (2018.01); *C12N 15/1137* (2013.01)

(58) Field of Classification Search
CPC ............................ A61K 31/519; A61P 11/00
See application file for complete search history.

(56) References Cited

U.S. PATENT DOCUMENTS

| | | | |
|---|---|---|---|
| 2012/0077828 A1* | 3/2012 | Axten | A61P 25/00 514/265.1 |
| 2013/0018038 A1* | 1/2013 | Axten | C07D 487/04 514/210.21 |

FOREIGN PATENT DOCUMENTS

| | | |
|---|---|---|
| WO | 2014/161808 A1 | 10/2014 |
| WO | 2015/191951 A2 | 12/2015 |
| WO | 2015/056180 A1 | 4/2019 |

OTHER PUBLICATIONS

Sun et al (Crit. Care Med. 41(12): pA46, 2013) (Year: 2013).*
Matsumoto et al (Biol Open. Aug. 27, 2013;2(10):1084-90) (Year: 2013).*
Lee et al (PloS ONE 5(5):e 10489, 8 pages, 2010) (Year: 2010).*
Boyle et al., "Pharmacological treatments in ARDS; a state-of-the-art update," BMC Med. 2013;11:166. PMID: 23957905. (Year: 2013).*
Li et al, Ulinastatin suppresses endoplasmic reticulum stress and apoptosis in the hippocampus of rats with acute paraquat poisoning, Neural regeneration research, Mar. 2015;10(3):467-472.
Axten et al., "Discovery of GSK2656157: An optimized PERK inhibitor Selected for Preclinical Development", ACS Med. Chem. Lett. 4(10), 964-968, 2013.
Cavanaugh et al., "Role of Stretch on Tight Junction Structure in Alveolar Epithelial Cells", Am J Respir Cell Mol Biol, 2001, 25, 584-591.
Chen et at, "Pulmonary permeability assessed by fluorescent-labeled dextran instilled intranasally into mice with LPS-induced acute lung injury", PLoS One, 2014, 9(7), e101925.
Cohen et al., "MAPk Activation Modulates Permeability of Isolated Rat Alveolar Epithelial Cell Monolayers Following Cyclic Stretch", PLoS One, 2010, 5, e10385.
Davidovich et al., "Cyclic stretch-induced oxidative stress increases pulmonary alveolar epithelial permeability", Am J Respir Cell Mol Biol, 2013, 49, 156-164.
Dolinay et al., "Inhaled Carbon monoxide confers anti-inflammatory effects against ventilator-induced lung injury", Am J Respir Crit Care Med, 2004, 170, 6, 613-620.
Dolinay et al., "Mitogen-activated protein kinases regulate susceptibility to ventilator-induced lung injury", PLoS One, 2008, e1601.
Ning et al., "Genome-wide analysis of the endothelial transcriptome under short-term chronic hypoxia", Physiol Genomics, 2004, 18, 70-78.

(Continued)

*Primary Examiner* — Theodore R. Howell
(74) *Attorney, Agent, or Firm* — BakerHostetler

(57) ABSTRACT

Disclosed herein are methods of preventing and/or treating lung injury and/or lung inflammation in a subject comprising administering to the subject a therapeutically effective dose of a PERK pathway inhibitor. Pharmaceutical compositions for the prevention and/or treatment of lung injury and/or lung inflammation comprising PERK pathway inhibitors are also provided. Also disclosed are uses of a PERK inhibitor in the manufacture of a medicament for the prevention and/or treatment of a lung injury and/or inflammation.

6 Claims, 35 Drawing Sheets

(56) References Cited

OTHER PUBLICATIONS

Song et al., "Local Influence of cell viability on stretch-induced permeability of alveolar epithelial cell monolayers", Cellular and molecular bioengineering, 2016, 9(1), 65-72.
Song et al., "Superoxide mediates tight junction complex dissociation in cyclically stretched lung slices", Journal of biomechanics, 2016, 49, 1330-1335.
Tschumperlin et al., "Equibiaxial deformation-induced injury of alveolar epithelial cells in vitro", Am J Physiol, 1998, 275.
Yerrapureddy et al., "Cyclic stretch magnitude and duration effect rat alveolar epithelial gene expression", Cellular physiology and biochemistry: international journal of experimental cellular physiology, biochemistry, and pharmacology, 2010, 25, 113-122.

\* cited by examiner

FIG. 19A    FIG. 19B
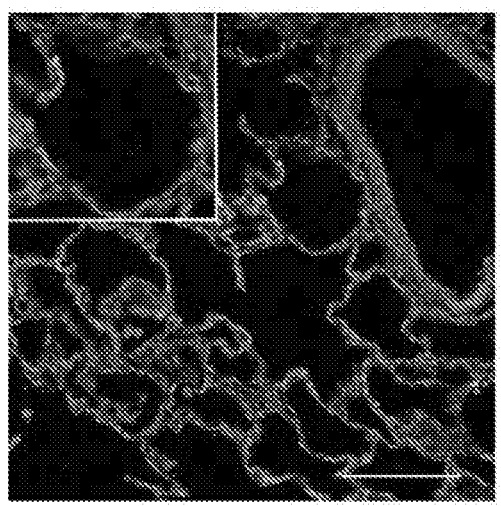 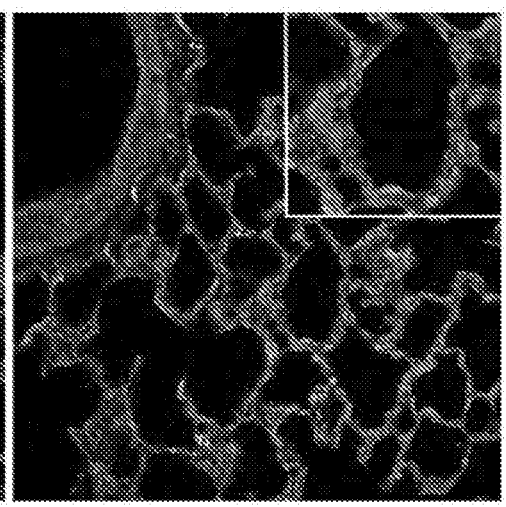
FIG. 19C
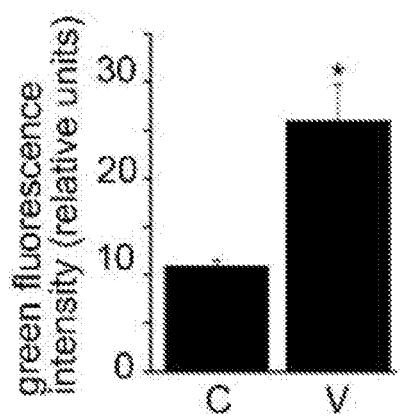
FIG. 19D
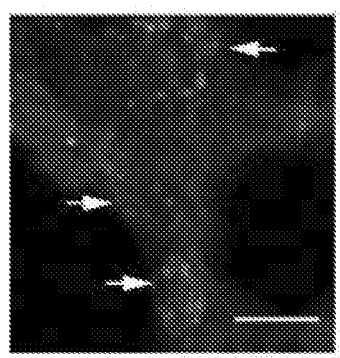

PROTEIN KINASE RNA-LIKE ENDOPLASMIC RETICULUM KINASE (PERK) INHIBITORS FOR PREVENTION AND/OR TREATMENT OF LUNG INJURY AND/OR INFLAMMATION

CROSS-REFERENCE TO RELATED APPLICATIONS

This application is the National Stage Application of International Patent Application No. PCT/US2017/029820 filed Apr. 27, 2017, which claims the benefit of U.S. Provisional Patent Application No. 62/329,955, filed Apr. 29, 2016, the entireties of which are incorporated by reference.

This application claims the benefit of U.S. Provisional Patent Application No. 62/329,955, filed Apr. 29, 2016, the entirety of which is incorporated by reference.

GOVERNMENT RIGHTS

This invention was made with government support under grant number 5T32HL007586 awarded by the National Institutes of Health. The Government has certain rights in the invention.

TECHNICAL FIELD

Disclosed herein are methods of preventing and/or treating lung injury and/or lung inflammation. In particular, the disclosed methods comprise the administration of a therapeutic agent to a subject that interferes with the PERK pathway.

BACKGROUND

Acute respiratory distress syndrome (ARDS) is a common and severe pulmonary complication of mechanical ventilation, characterized by damage to the epithelial barrier due to alveolar overdistention with subsequent pulmonary edema and profound hypoxia. In the intensive care unit, 10 to 15% of all ventilated patients have ARDS, with associated mortality rates of nearly 40%. Available lung protective ventilator strategies have only modest benefit on ARDS because they cannot prevent alveolar overdistention in the lung tissue adjacent to the inflamed lung regions. Furthermore, biochemical blockade of mediator release from inflammatory cells in ARDS has not yielded in significant clinical benefit. Currently there are no effective biochemical therapies to mitigate injury to the alveolar epithelium.

SUMMARY

Disclosed herein are methods of preventing and/or treating lung injury and/or lung inflammation in a subject comprising administering to the subject a therapeutically effective dose of a PERK pathway inhibitor to prevent and/or treat the lung injury and/or lung inflammation.

Pharmaceutical compositions for the prevention and/or treatment of lung injury and/or lung inflammation comprising PERK pathway inhibitors are also provided.

Further provided is the use of a PERK inhibitor in the manufacture of a medicament for the prevention and/or treatment of a lung injury and/or lung inflammation, as well as PERK inhibitors for use in the prevention and/or treatment of lung injury and/or lung inflammation.

BRIEF DESCRIPTION OF THE DRAWINGS

The summary, as well as the following detailed description, is further understood when read in conjunction with the appended drawings. For the purpose of illustrating the disclosed methods, pharmaceutical compositions, and uses, there are shown in the drawings exemplary embodiments of the methods, pharmaceutical compositions, and uses; however, the methods, pharmaceutical compositions, and uses are not limited to the specific embodiments disclosed. In the drawings:

FIG. 3F illustrates that PI pretreatment significantly reduced monolayer permeability measured with FITC-labeled streptavidin binding to biotin. FIG. 3G illustrates that decreased stretch-induced cell death was detected in monolayers pre-treated with PI. NS=no stretch, NSPI=no stretch+ PERK inhibitor (PI), S=stretch, SPI=stretch+PI. *represents significant difference between NS and S or SPI conditions. # represents significant difference between S and SPI conditions, p<0.05. N=6-8 biological monolayer replicates/ condition.

FIG. 4A-FIG. 4C illustrate that increased interleukin-18 (IL-18), interleukin-1α (IL-1α) and macrophage inflammatory protein-1α (MIP-1α) levels, respectively, were detected in the supernatant of stretch monolayers. PI treatment decreased IL-18 levels but did not affect IL-1α and MIP-1α. D. siRNA was used to inhibit ISR signaling in stretched (S) and unstretched (NS) monolayers (0.5 µg siRNA, 24 hours pretreatment). CHOP inhibition (siRNA/CHOP) decreased CHOP expression but did not affect ATF4. ATF4 inhibition (siRNA/ATF4) resulted in partial reduction in both CHOP and ATF4. Transfection reagent (VC) and non-targeting siRNA (siRNA/NT) served as controls. Protein expression was normalized to 3-actin and quantified using densitometry. Quantified densities are shown in FIG. 4E-FIG. 4F. FIG. 4G illustrates that CHOP, ATF4 and PERK knockdown significantly decreased the IL-18 levels measured in the supernatant of stretched monolayers. Statistics: Kruskal-Wallis test was used for multiple group comparison, and intergroup differences were analyzed with Wilcoxon rank sum test. For cytokine studies, N=8-9 biological monolayer replicates/condition. For siRNA experiments, N=4-5 biological monolayer replicates/condition. For FIG. 4A-FIG. 4C: *represents significant increase in cytokine levels NS versus S and # represents significant decrease between S and SPI conditions. For FIG. 4E-4F: *represents significant increase in protein expression in NS versus S conditions. # represents significant decrease in ATF4 and CHOP protein expression when compared to the siRNA/NT condition in unstretched monolayers. $ represents significant decrease in ATF4 and CHOP expression compared to the siRNA/NT condition in stretched monolayers. For FIG. 4G: *represents significant increase in IL-18 levels in S versus NS conditions. # represents significant decrease in IL-18 levels in siRNA/CHOP, siRNA/ATF4 and siRNA/PERK conditions versus siRNA/NT. Significance level was set at p<0.05 for all experiments.

In FIG. 6A-FIG. 6D, rats were treated with 30 mg/kg GSK2606414 compound (PI) or its vehicle (0.1% TWEEN 80 in 0.5% hydroxyethyl-methylcellulose) via oral gavage. Four hours later the animals were anesthetized and mechanically ventilated (V) as previously described or allowed to breathe spontaneously (C). PI treatment (VPI) significantly reduced VILI-mediated phosphorylation of EIF2α and the protein expression of ATF4 and CHOP but did not affect controls (CPI). FIG. 6E illustrates that VILI increased BAL total protein content, suggesting increased alveolo-capillary permeability and pulmonary edema formation. PI pretreated animals were protected from VILI-induced permeability increase. In FIG. 6F, Alveolo-capillary barrier dysfunction in VILI was confirmed with FITC-labeled albumin extravasation to the alveoli. VPI animals showed decreased FITC-labeled albumin permeability index when compared to V. FIG. 6G, illustrates the composite lung injury score calculated for all animals. PI pretreatment mitigated lung injury score in ventilated animals. FIG. 6H illustrates that VILI significantly increased proinflammatory cytokine IL-18 levels in the BAL. PI pre-treated animals exhibited reduced IL-18 BAL levels. FIG. 6I, illustrates that serum IL-18 levels also increased in the serum of ventilated animals but PI did not affect its levels. PI treatment significantly decreased BAL total cell count (FIG. 6J) and neutrophil cell count (FIG. 6K) Statistics: Kruskal-Wallis test was performed for multiple group comparison, and intergroup differences were analyzed with Wilcoxon rank sum test. N=5-9 animals/condition. *represents significant increase in V vs. C conditions and # represents significant decrease in VPI vs. V conditions, p<0.05.

FIG. 12A shows control; FIG. 12B shows mechanical ventilation. Mechanical ventilation increases EIF2a phosphorylation in alveolar epithelial cells. Scale bar=50 µM.

FIG. 16A illustrates the results from monolayers subjected to biaxial stretch for 6 hours with 25% surface change (S) and compared to unstretched controls (NS). Low dose tunicamycin (TN, 1 µg/ml, 24 hours treatment) was used as a positive control and parameters were compared to DMSO-treated (0.01%) unstretched vehicle controls (VC). Mechanical stretch significantly increased the phosphorylation of protein kinase RNA-like endoplasmic reticulum kinase (p-PERK), which resulted in activation of ISR marked by eukaryotic initiation factor-2α phosphorylation (p-EIF2α) and the activation of activating transcription factor 4 (ATF4) and CCAAT/Enhancer-binding protein homologous protein (CHOP). Mechanical stretch did not affect IRE1α phosphorylation (p-IRE1α) or its downstream transcription factor X-box binding protein 1 (XBP1) activation. Quantified densities are shown in FIG. 16B-FIG. 16G. *represents significant increase in protein phosphorylation (FIG. 16B, FIG. 16C, FIG. 16F), and protein expression (FIG. 16D, FIG. 16E, FIG. 16G), p<0.05. Data is presented as averaged values ±SEM.

FIG. 17A illustrates the results from AEC-I monolayers transfected with non-targeting (siRNA/NT) or PERK specific (siRNA/PERK) siRNA (0.5 µg, 24 hours treatment) and subjected to cyclic mechanical stretch (25% surface change for 6 hours). Unstretched monolayers served as controls. FIG. 17B illustrates that PERK knockdown resulted in significant t-PERK expression decrease. To measure monolayer permeability, cells were cultured on silastic membranes were coated with biotinylated fibronectin. After the study, the membranes were stained with FITC-labeled streptavidin. Under unstretched conditions the monolayer is impermeable to large molecules, which prevents streptavidin-biotin binding. Stretch resulted in cell-cell contact disruption and subsequent binding of streptavidin to the membrane-bound biotin, which was detected with fluorescent microscopy (FIG. 17C). PERK inhibition resulted in decreased monolayer permeability. For densitometry data analysis Kruskal-Wallis test was performed for multiple group comparison and intergroup differences were analyzed with Wilcoxon rank sum test. For permeability studies, one-way ANOVA with post hoc Dunnett's test was used and for multiple conditions two-way ANOVA was performed with Tukey-Kramer post hoc analysis. *represents significant change between siRNA/NT and siRNA/PERK conditions (FIG. 17B) and NS and S conditions (FIG. 17C). # represents significant decrease between siRNA/NT and siRNA/PERK S conditions, p<0.05. N=4 biological monolayer replicates/condition.

FIG. 19A-FIG. 19D shows that injurious mechanical ventilation increased EIF2α phosphorylation in vivo. The fluorescent light emission of Alexa Fluor 488-labeled p-EIF2α antibody staining was compared between lung tissues obtained from spontaneously breathing (FIG. 19A) and mechanically ventilated (FIG. 19B) rats (20 ml/kg tidal volume ventilation without positive end expiratory pressure for 4 hours via tracheostomy). EIF2α staining was present in multiple alveolar cell types including AEC-I cells labeled with occludin. Scale bar=100 µm. Inserts show 100 µm enlarged areas. Quantified confocal images showed significant p-EIF2α increase in ventilated rats (V) when compared to spontaneously breathing controls (FIG. 19C). Enlarged epithelial cells with arrows pointing at intracellular p-EIF2α staining are shown in FIG. 19D. Scalebar=10 µm. Statistics: two-way ANOVA. * represents significant increase C versus V conditions, p<0.05, N=3 biological replicates/condition and 5 images/biological replicates.

As shown in FIG. 22B-FIG. 22E, stretch significantly enhanced the dissociation of claudin (CLDN) 4 and 18, but did not alter CLDN7 and occludin (OCLN) binding to ZO-1. PI treatment prevented the dissociation of CLDN 4 and 18 from ZO-1. Quantified densitometry data of CLDN and OCLN expression levels is shown normalized to ZO-1. * represents significant decrease between NS and S conditions. # represents significant increase between S and SPI conditions. P<0.05, Kruskal-Wallis Test, N=4 biological replicates/condition.

DETAILED DESCRIPTION OF ILLUSTRATIVE EMBODIMENTS

Figure 1:
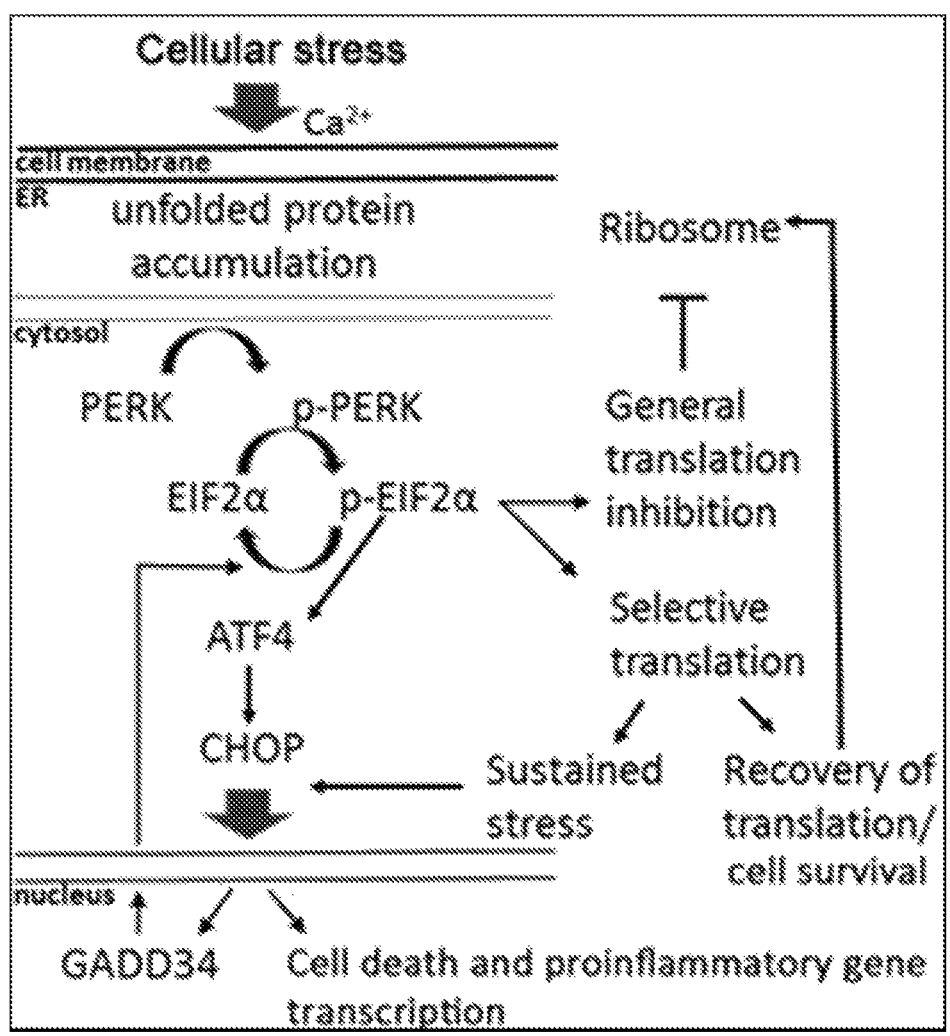
FIG. 1 illustrates the unfolded protein response-induced ISR activation by PERK.

The disclosed methods, pharmaceutical compositions, and uses may be understood more readily by reference to the following detailed description taken in connection with the accompanying figures, which form a part of this disclosure. It is to be understood that the disclosed methods, pharmaceutical compositions, and uses are not limited to the specific methods, pharmaceutical compositions, and uses described and/or shown herein, and that the terminology used herein is for the purpose of describing particular embodiments by way of example only and is not intended to be limiting of the claimed methods, pharmaceutical compositions, and uses.

Unless specifically stated otherwise, any description as to a possible mechanism or mode of action or reason for improvement is meant to be illustrative only, and the disclosed methods, pharmaceutical compositions, and uses are not to be constrained by the correctness or incorrectness of any such suggested mechanism or mode of action or reason for improvement.

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value. All ranges are inclusive and combinable.

The term "about" when used in reference to numerical ranges, cutoffs, or specific values is used to indicate that the recited values may vary by up to as much as 10% from the listed value. As many of the numerical values used herein are experimentally determined, it should be understood by those skilled in the art that such determinations can, and often times will, vary among different experiments. The values used herein should not be considered unduly limiting by virtue of this inherent variation. Thus, the term "about" is used to encompass variations of 10% or less, variations of 5% or less, variations of 1% or less, variations of +0.5% or less, or variations of +0.1% or less from the specified value.

It is to be appreciated that certain features of the disclosed methods, pharmaceutical compositions, and uses which are, for clarity, described herein in the context of separate embodiments, may also be provided in combination in a single embodiment. Conversely, various features of the disclosed methods, pharmaceutical compositions, and uses that are, for brevity, described in the context of a single embodiment, may also be provided separately or in any subcombination.

As used herein, the singular forms "a," "an," and "the" include the plural.

Various terms relating to aspects of the description are used throughout the specification and claims. Such terms are to be given their ordinary meaning in the art unless otherwise indicated. Other specifically defined terms are to be construed in a manner consistent with the definitions provided herein.

The term "comprising" is intended to include examples encompassed by the terms "consisting essentially of" and "consisting of." The term "consisting essentially of" is intended to include examples encompassed by the term "consisting of."

The term "pharmaceutically acceptable" refers to a compound, additive or composition that is not biologically or otherwise undesirable. For example, the additive or composition may be administered to a subject along with the disclosed therapeutic agent that interferes with the PERK pathway without causing any undesirable biological effects or interacting in an undesirable manner with any of the other components of the pharmaceutical composition in which it is contained. Whether a compound, additive or composition is "pharmaceutically acceptable" can be dependent upon factors well-known in the medical field, such as the kind of disease, age, body weight, health status, sex, drug sensitivity of a patient, administration route, administration method, administration frequency, duration of treatment, and drug(s) to be mixed or administered simultaneously in combination.

The term "subject" as used herein is intended to mean any animal, in particular, mammals. Thus, the methods are applicable to human and nonhuman animals, although preferably used with mice and humans, and most preferably with humans. "Subject" and "patient" are used interchangeably herein.

As used herein, the phrase "therapeutically effective amount" refers to an amount of the therapeutic agent that interferes with the PERK pathway, as described herein, effective to achieve a particular biological or therapeutic result such as, but not limited to, biological or therapeutic results disclosed, described, or exemplified herein. The therapeutically effective amount may vary according to factors such as the disease state, age, sex, and weight of the individual, and the ability of the composition to cause a desired response in a subject. Exemplary indicators of a therapeutically effect amount include, for example, improved well-being of the patient, prevention of lung injury and/or lung inflammation, and treatment of lung injury and/or lung inflammation.

The following abbreviations are used throughout the disclosure: Acute respiratory distress syndrome (ARDS); Activating Transcription Factor 4 (ATF4); CCAAT/Enhancer-Binding Protein Homologous Protein (CHOP); Integrated Stress Response (ISR); Protein Kinase RNA-like Endoplasmic Reticulum Kinase (PERK); ventilator-induced lung injury (VILI).

Disclosed herein are methods of preventing and/or treating lung injury and/or lung inflammation in a subject comprising administering to the subject a therapeutically effective dose of a PERK pathway inhibitor to prevent and/or treat the lung injury and/or inflammation. In some aspects, the disclosed methods can be used to prevent lung injury and/or lung inflammation in a subject. In some aspects, the disclosed methods can be used to treat lung injury and/or lung inflammation in a subject. In some aspects, the disclosed methods can be used to prevent and treat lung injury and/or lung inflammation in a subject.

The terms "treating" or "treatment," used synonymously with "therapy," refer to an approach for obtaining beneficial or desired results including but not limited to therapeutic benefit. Therapeutic benefit includes the eradication or amelioration of the underlying disorder being treated, reducing the severity and/or frequency of symptoms, eliminating symptoms and/or the underlying cause of the symptoms, reducing the frequency or likelihood of symptoms and/or their underlying cause, and improving or remediating damage caused, directly or indirectly, by the mechanical ventilator. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. Treatment also includes prolonging survival as compared to the expected survival of a subject not receiving treatment the compositions may be administered to a patient reporting one or more of the physiological symptoms of a disease, even though a diagnosis of this disease may not have been made.

As used herein, "prevent", "preventing" or "prevention" refers to an approach for obtaining beneficial or desired results including a prophylactic benefit. The compositions may be administered to a patient at risk of developing a particular disease (ventilator-induced lung injury, for example). Patients in whom prevention can be used include those prone to have the condition or disorder.

Lung injury, as used herein, includes, but is not limited to, acute respiratory distress syndrome or ventilator-induced lung injury. Thus, in some embodiments, the disclosed methods can be used to prevent and/or treat acute respiratory distress syndrome. In other embodiments the disclosed methods can be used to prevent and/or treat ventilator-induced lung injury.

As used herein, "PERK inhibitor" includes agents that inhibit, reduce, or otherwise decrease the activity of or signaling through the Protein Kinase RNA-like Endoplasmic Reticulum Kinase (PERK) pathway. An exemplary PERK pathway is illustrated in FIG. 1.

Suitable PERK inhibitors include, but are not limited to, small molecules or siRNA. In some embodiments, the PERK inhibitor comprises a small molecule. Thus, the methods of preventing and/or treating lung injury and/or lung inflammation in a subject can comprise administering to the subject a small molecule. In other embodiments, the PERK inhibitor comprises a siRNA. Thus, the methods of preventing and/or treating lung injury and/or lung inflammation in a subject can comprise administering to the subject a siRNA. In some embodiments, the siRNA inhibits expression of a nucleic acid encoding CHOP, ATF-4 or PERK.

The PERK inhibitor can be a small molecule. In some embodiments, the PERK inhibitor can be 1-[5-(4-Amino-7-methyl-7H-pyrrolo[2,3-d]pyrimidin-5-yl)indolin-1-yl]-2-(3-trifluoromethylphenyl)ethanone. For example, the PERK inhibitor can be GSK2606414 having the following structure:

(Formula I)

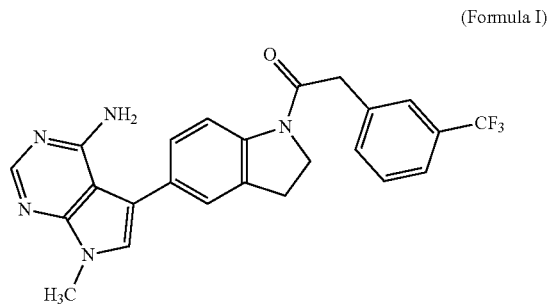 [SMILES: Cn1cc(-c2ccc3c(c2)CCN3C(=O)Cc2cccc(C(F)(F)F)c2)c2c(N)ncnc21]

Suitable PERK inhibitors also include those disclosed in Int'l Pub. No. WO2015/056180 and Int'l Pub. No. WO2014/161808.

Accordingly, in some embodiments, the methods of preventing and/or treating lung injury and/or lung inflammation in a subject comprise administering to the subject a PERK inhibitor, wherein the PERK inhibitor has the structure of formula I.

Also provided are pharmaceutical compositions for the prevention and/or treatment of lung injury and/or lung inflammation comprising PERK pathway inhibitor. In some embodiments, the pharmaceutical composition can further comprise a pharmaceutically acceptable carrier.

Lung injuries and/or lung inflammation and suitable therapeutic agents can be the same as those disclosed above. Thus, in some embodiments, the pharmaceutical compositions can be used to prevent and/or treat acute respiratory distress syndrome. In other embodiments, the pharmaceutical compositions can be used to prevent and/or treat ventilator-induced lung injury.

The PERK pathway inhibitor can be small molecules or siRNA. In some embodiments, the pharmaceutical composition comprises a small molecule as the therapeutic agent. In other embodiments, the PERK pathway inhibitor comprises a siRNA as the therapeutic agent. In some embodiments, the siRNA inhibits expression of a nucleic acid encoding CHOP, ATF-4 or PERK.

The small molecule can be a PERK inhibitor. In some embodiments, the PERK inhibitor can be 1-[5-(4-Amino-7-methyl-7H-pyrrolo[2,3-d]pyrimidin-5-yl)indolin-1-yl]-2-(3-trifluoromethylphenyl)ethanone. For example, the PERK inhibitor can be GSK2606414 having the following structure of Formula I.

Also provided is the use of a PERK inhibitor in the manufacture of a medicament for the prevention and/or treatment of a lung injury and/or lung inflammation. The PERK inhibitor can be 1-[5-(4-Amino-7-methyl-7H-pyrrolo[2,3-d]pyrimidin-5-yl)indolin-1-yl]-2-(3-trifluoromethylphenyl)ethanone. For example, the PERK inhibitor can be GSK2606414 having the structure of Formula I.

Further disclosed are PERK inhibitors for use in the prevention and/or treatment of lung injury and/or lung inflammation. The PERK inhibitor can be 1-[5-(4-Amino-7-methyl-7H-pyrrolo[2,3-d]pyrimidin-5-yl)indolin-1-yl]-2-(3-trifluoromethylphenyl)ethanone. For example, the PERK inhibitor can be GSK2606414 having the structure of Formula I.

EXAMPLES

The following examples are provided to further describe some of the embodiments disclosed herein. The examples are intended to illustrate, not to limit, the disclosed embodiments.

The Functional Role of ISR Pathway in Mechanical Stretch-Induced AEC-I Cell Injury Using the established stretched primary Type I-like rat alveolar epithelial cell (RAEC-I) monolayer (described in Cavanaugh et al. Role of Stretch on Tight Junction Structure in Alveolar Epithelial Cells. Am J Respir Cell Mol Biol 2001; 25: 584-591; and Cohen et al. MAPk Activation Modulates Permeability of Isolated Rat Alveolar Epithelial Cell Monolayers Following Cyclic Stretch PLoS One. 2010; 5: e10385) and ventilated rat preparations (described in Dolinay et al. Carbon monoxide confers anti-inflammatory effects against ventilator-induced lung injury. Am J Respir Crit Care Med. 2004; 170: 6: 613-620; and Davidovich et al. Cyclic stretch-induced oxidative stress increases pulmonary alveolar epithelial permeability Am J Respir Cell Mol Biol 2013; 49:156-164) which mimic ventilator-induced lung injury (VILI), the role of the intracellular Integrated Stress Response (ISR) signaling pathway activation in stretch-induced increases in epithelial permeability was evaluated. The ISR regulates the cell's protein translation and survival response to environmental stressors. It is most well described as part of the unfolded protein response (UPR) in eukaryotic cells. UPR accumulation results in PERK auto-phosphorylation and subsequent Eukaryotic initiation factor 2a phosphorylation (p-EIF2α) which leads to general protein translation inhibition on the ribosome. Parallel activation of Activating transcription factor 4 (ATF4) and CCAAT/Enhancer-binding protein homologous protein (CHOP) gene transcription by p-EIF2α exerts pro-cell survival or pro-cell death signaling depending on the length of stress. Protein translation is recovered by EIF2α dephosphorylation via Growth arrest and DNA damage-inducible protein 34 (GADD34). ER=endoplasmatic reticulum (FIG. 1).

Mechanical Stretch Activates ISR and Cell Death in AEC-I

Figure 8:
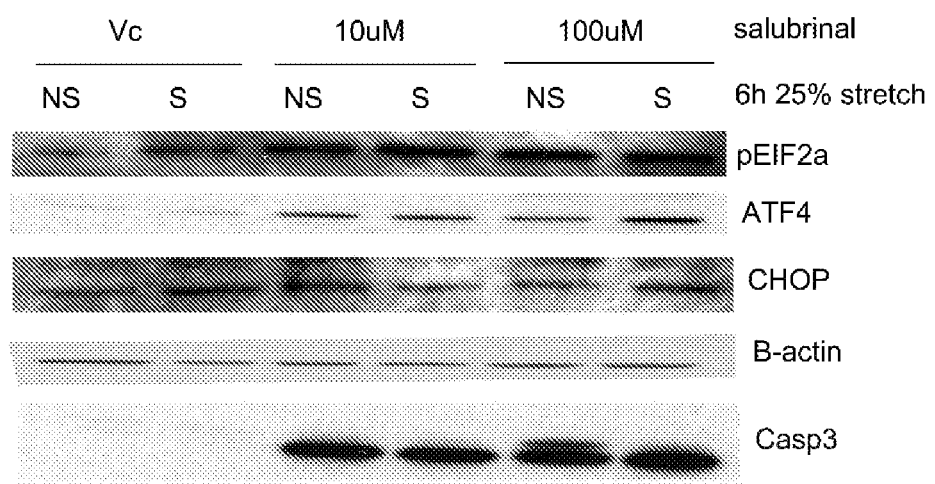
FIG. 8 illustrates that EIF2a dephosphorylation inhibition increases ISR and apoptosis in mechanically stretched epithelium.
Figure 16A:
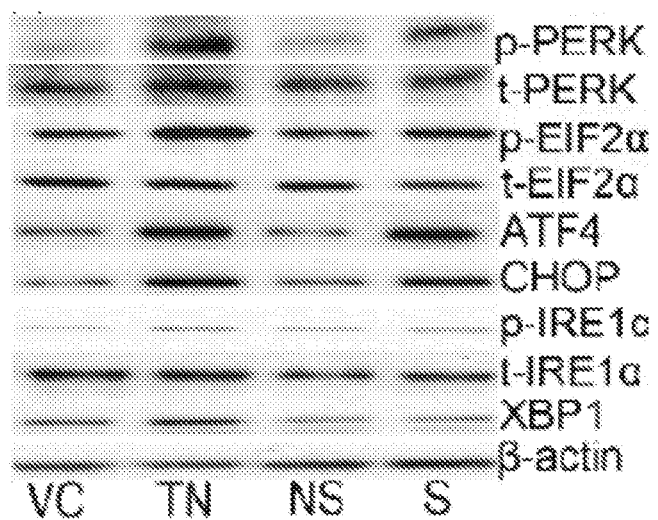
FIG. 16A-FIG. 16G shows that mechanical stretch activates integrated stress response (ISR) signaling independent of inositol-requiring protein-1α (IRE1α) pathway in primary alveolar type-I like epithelial cells (AEC-I). AEC-I cells were cultured on silastic membranes coated with fibronectin to form monolayers.
Figure 16B:
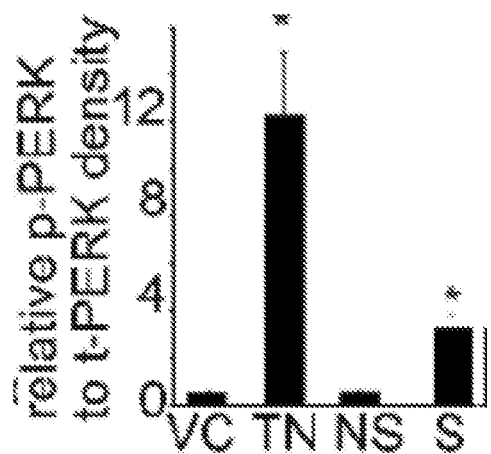
Figure 16C:
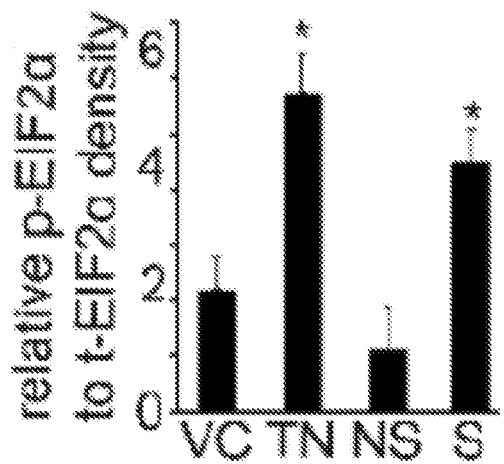
Figure 16D:
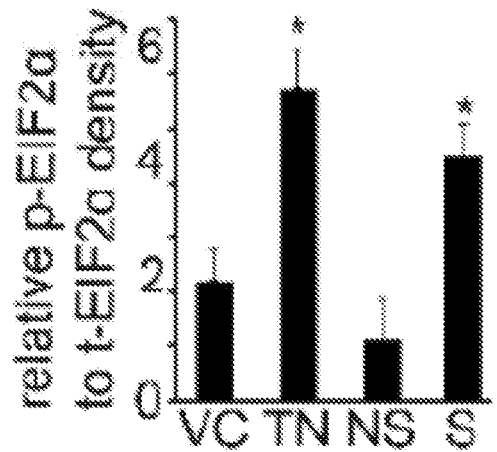
Figure 16E:
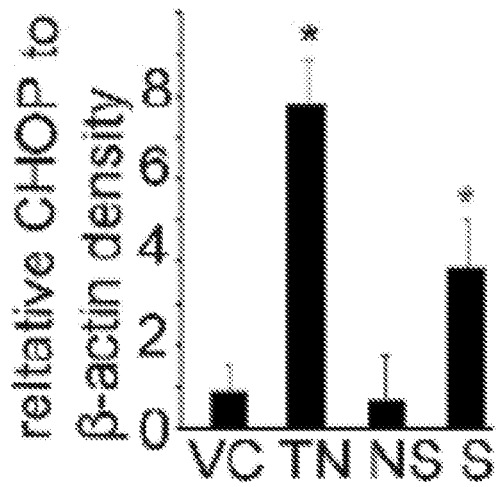
Figure 16F:
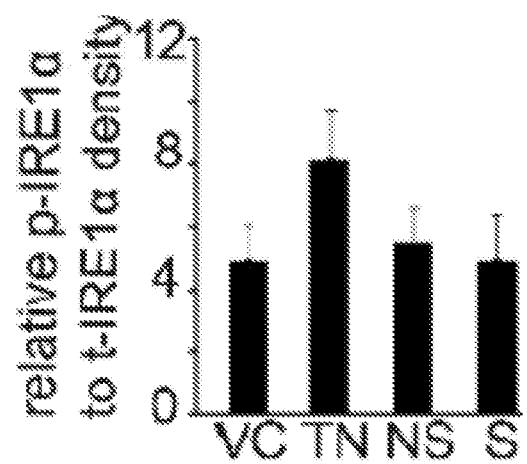
Figure 16G:
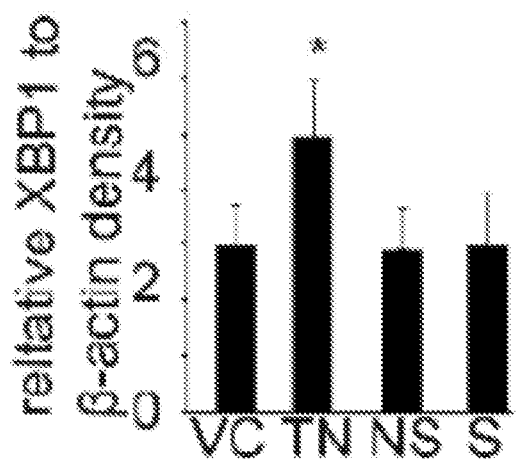

To study epithelial stress signaling in response to mechanical stretch, the mechanism of ATF4 and CHOP activation in the in vitro cell stretch model was investigated. The phosphorylation of PERK and EIF2α as well as the expression of ATF4 and CHOP was compared between stretched and unstretched monolayers. tunicamycin (1 µg/ml pretreatment for 24 hours), a canonical activator of cell stress signals, was used as a positive control to benchmark the magnitude of ISR activation by mechanical stretch. Cyclic stretch resulted in increased PERK, EIF2α phosphorylation and subsequent ISR signaling similar to what is seen with tunicamycin (FIG. 16A-FIG. 16E). To evaluate the role of PERK independent stress signaling in the model, IRE-1α phosphorylation and the activation of its downstream transcription factor, factor X-box binding protein-1 (XBP1) were measured. Mechanical stretch did not increase IRE-1α phosphorylation or XBP1 expression (FIG. 16A, FIG. 16E-FIG. 16F). ISR activation in response to tunicamycin and stretch were not related to increased cell death measured with cleaved caspase 3 (Casp3) immunoblotting (FIG. 7A-FIG. 7E). However ISR activation by EIF2α dephosphorylation inhibition with salubrinal (Sal) resulted in significant increase in Casp3 levels in unstretched and stretched monolayers suggesting that persistently high EIF2α levels result in cell death (FIG. 8).

Figure 2A:
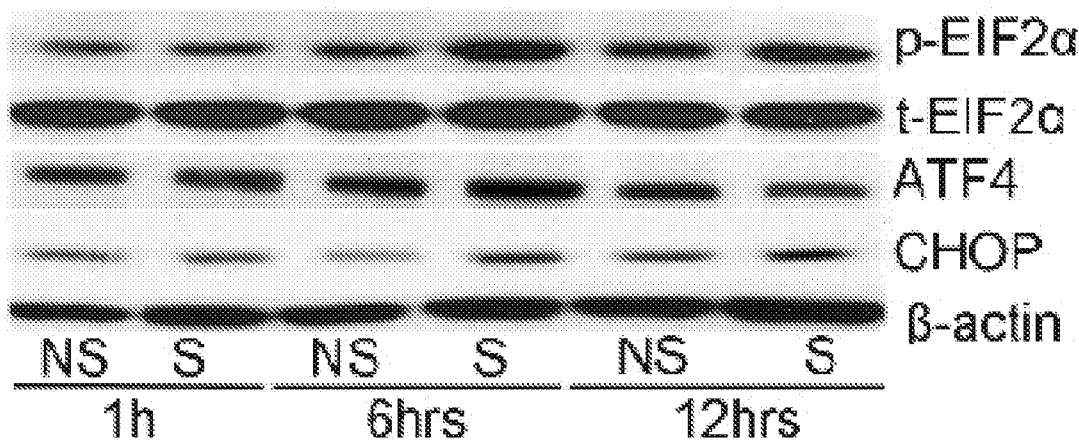
FIG. 2A illustrates that mechanical stretch activates ISR in a time dependent fashion in AEC-I monolayers. Time-dependent increases in p-EIF2α, ATF4 and CHOP following biaxial mechanical stretch were detected with 25% surface change for 1 to 12 hours. Maximum changes were observed at 6 hours. Quantified densities are shown in FIG. 2B-FIG. 2D.
Figure 2B:
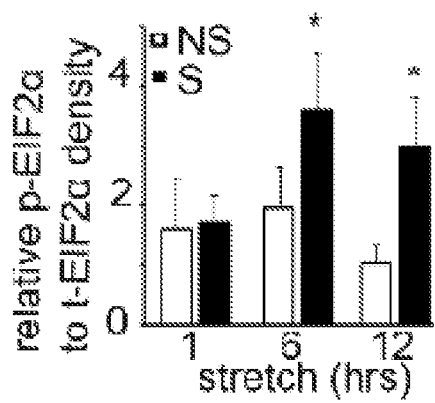
FIG. 2E illustrates that only a mild increase in cell death was detected at 6 hours with ethidium homodimer staining, but it increased to high levels by the 12 hour time point. Total (t)-PERK, t-EIF2α, t-IRE1α and β-actin was used as loading controls. Statistics: Kruskal-Wallis test was performed for multiple group comparison, and intergroup differences were analyzed with Wilcoxon rank sum test. N=6-8 biological monolayer replicates/condition. NS=no stretch, S=stretch. *represents significant increase in protein phosphorylation (FIG. 2B), protein expression (FIG. 2C-FIG. 2D) and in cell death percent (FIG. 2E) (p<0.05) between NS and S conditions. Data is presented as averaged values ±SEM. The same abbreviations will be used in subsequent figures.
Figure 2C:
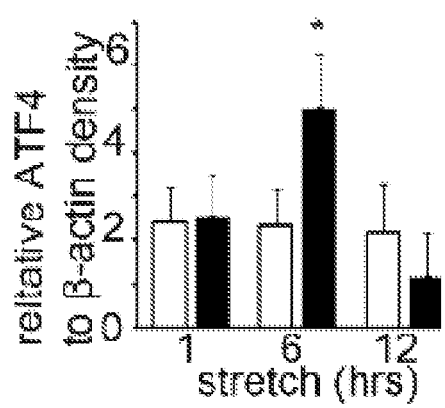
Figure 2D:
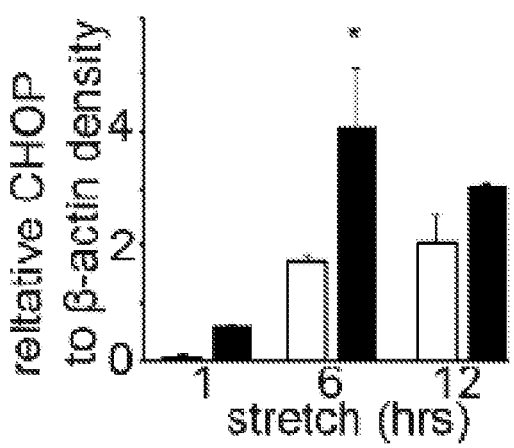
Figure 2E:
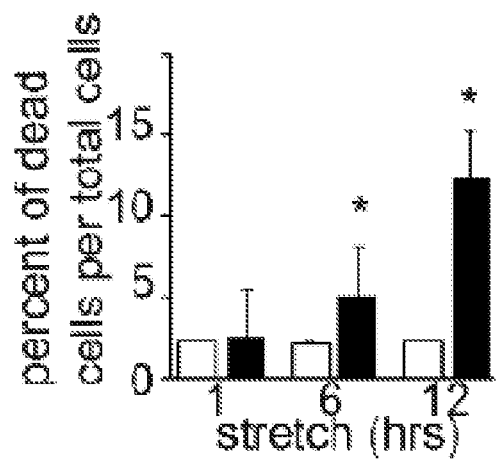
Figures 10A, 10B:
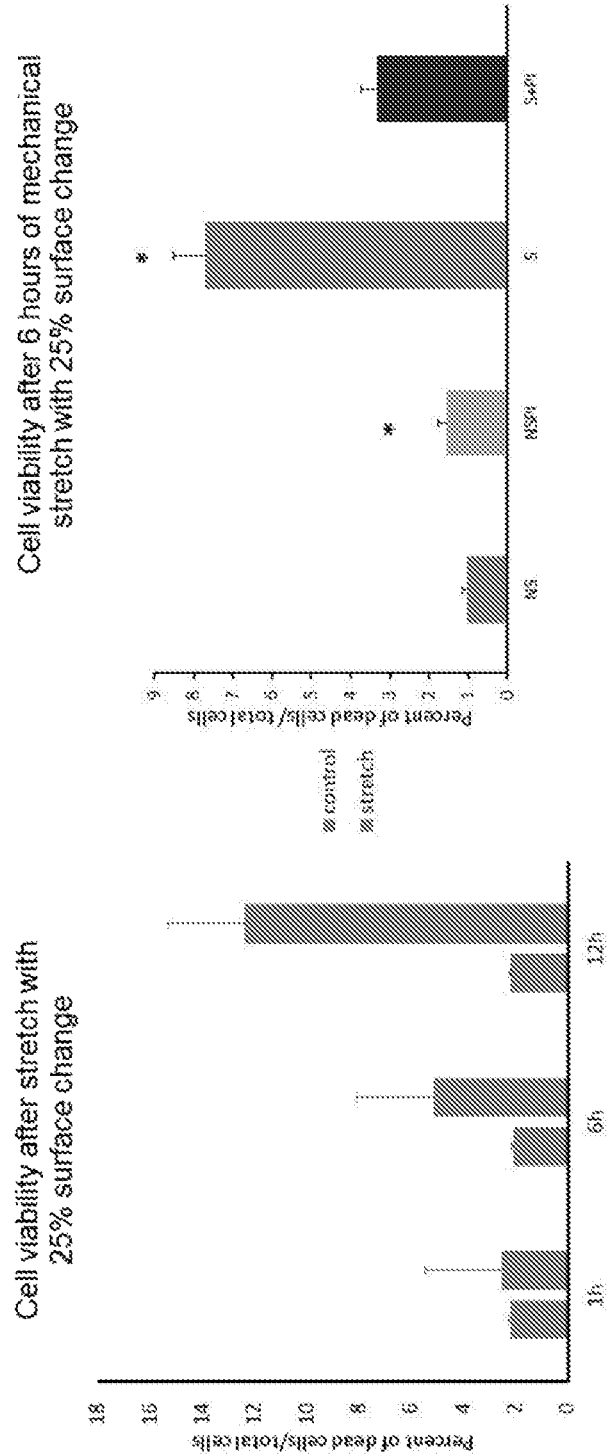
FIG. 10A-FIG. 10B illustrate that PERK inhibition mitigates mechanical stretch-induced cell death. N=3 independent experiments, *P<0.05 NS vs. treatment, # p<0.05 S vs. S+PI, t-test FIG. 11A

To study the time course of ISR activation, AEC-I cell monolayers were exposed to 25% biaxial cyclic stretch for 1 to 12 hours. EIF2α phosphorylation and protein expression of ATF4 and CHOP were compared between stretched cell monolayers (S) non-stretch controls (NS). As shown in FIG. 2A-FIG. 2D, mechanical stretch activated ISR in a time dependent manner by increasing p-EIF2α, ATF4 and CHOP significantly by 6 hours. To assess cellular death-mediated ISR activation, monolayers were stained with ethidium homodimer. Substantial cell death was not detected before 12 hours (FIG. 2E and FIG. 10A). These findings suggest that the PERK/p-EIF2α/ATF4/CHOP cascade is stretch-induced transmitter of mechanical stress signals in the epithelium.

Gene Expression Profiling in Stretch-Induced Epithelial Injury

To identify genes and associated intracellular pathways that mediate injury signaling in the alveolar epithelium, QuantSeq was used to compare the gene expression profile of mechanically stretched AEC-I monolayers to that of unstretched controls. Cells were exposed to biaxial cyclic (15/min) stretch for 6 hours with 25% surface area change. This stretch magnitude corresponds to 80% increase in total rat lung capacity, or 15 ml/kg positive pressure mechanical ventilation.

Gene ontology (GO) enrichment analysis of the 924 differentially expressed genes showed that AEC-I cells respond to mechanical stretch primarily by regulating genes of cellular stress pathways (Table 1). The GO categories shown in Table 1 are significantly enriched with genes following mechanical stretch (S) when compared to unstretched (NS) controls. Representative genes of interest with fold change stretch S vs. NS in expression are shown in Table 1. Significance analysis was performed with DESeq2 program package, adjusted p-value <0.05. GO functional grouping was performed with NIH DAVID. N=5 biological replicates/condition.

TABLE 1

| Gene ontology category [$] | Percent of significant genes (%) | Genes of example in functional groups[&] | Fold change (S/NS) |
|---|---|---|---|
| Cation binding | 18.75 | Rhobtb1 | 0.51 |
| Nuclear lumen | 7.8 | Areg | 1.77 |
| Cell death | 7.57 | Gadd45 | 0.35 |
| Regulation of transcription | 6.73 | Atf4 | 1.94 |
|  |  | Ddit3 (Chop) | 1.75 |
| mRNA processing | 1.92 | Ccl3 (Mip1a) | 3.9 |
|  |  | Il1a | 2.55 |
|  |  | Il1b | 1.97 |
| Steroid metabolism | 1.08 | Ptgs2 (Cox2) | 3.36 |
| Protein kinase activity | 0.96 | Map3k8 | 2.68 |
| Epithelial to mesenchymal transition | 0.6 | Cldn18 | 0.57 |
|  |  | Cldn23 | 0.5 |
|  |  | Cldn1 | 1.54 |

[$] Functional groups significantly enriched in genes are shown.
[&] Representative genes of interest with fold change (S/NS ratio) in expression are shown.

Among these genes were Atf4 and Chop (aka DNA damage inducible transcript 3, Ddit3) two transcription factors of the ISR pathway. The ISR pathway is a central integrator of cellular stress responses, and it has been implicated in the pathology of lung diseases. To validate the increase in mRNA expression that was observed in Atf4 and Chop, results were obtained from previous microarray studies performed on stretched AEC-I (25% surface area change for 6 hours) and on mouse lungs ventilated with 10 ml/kg positive pressure and 2 cmH2O positive end expiratory pressure (PEEP) for 8 hours. Both mechanical stretch and mechanical ventilation resulted in significantly increased mRNA expression of Atf4 (2.4- and 1.6-fold, respectively) and Chop (5.0- and 1.8-fold, respectively) compared to untreated controls (adjusted p-value<0.05; statistical analysis was performed with ANOVA and Welch's two sample t-test, respectively). (Yerrapureddy A, Tobias J, Margulies SS. Cyclic stretch magnitude and duration affect rat alveolar epithelial gene expression. *Cellular physiology and biochemistry: international journal of experimental cellular physiology, biochemistry, and pharmacology* 2010; 25:113-122; and Dolinay T, Wu W, Kaminski N, Ifedigbo E, Kaynar A M, Szilasi M, Watkins S C, Ryter S W, Hoetzel A, Choi A M. Mitogen-activated protein kinases regulate susceptibility to ventilator-induced lung injury. *PLoS ONE* 2008; 3:e1601).

PERK Inhibition Improves Barrier Function

Figure 9:
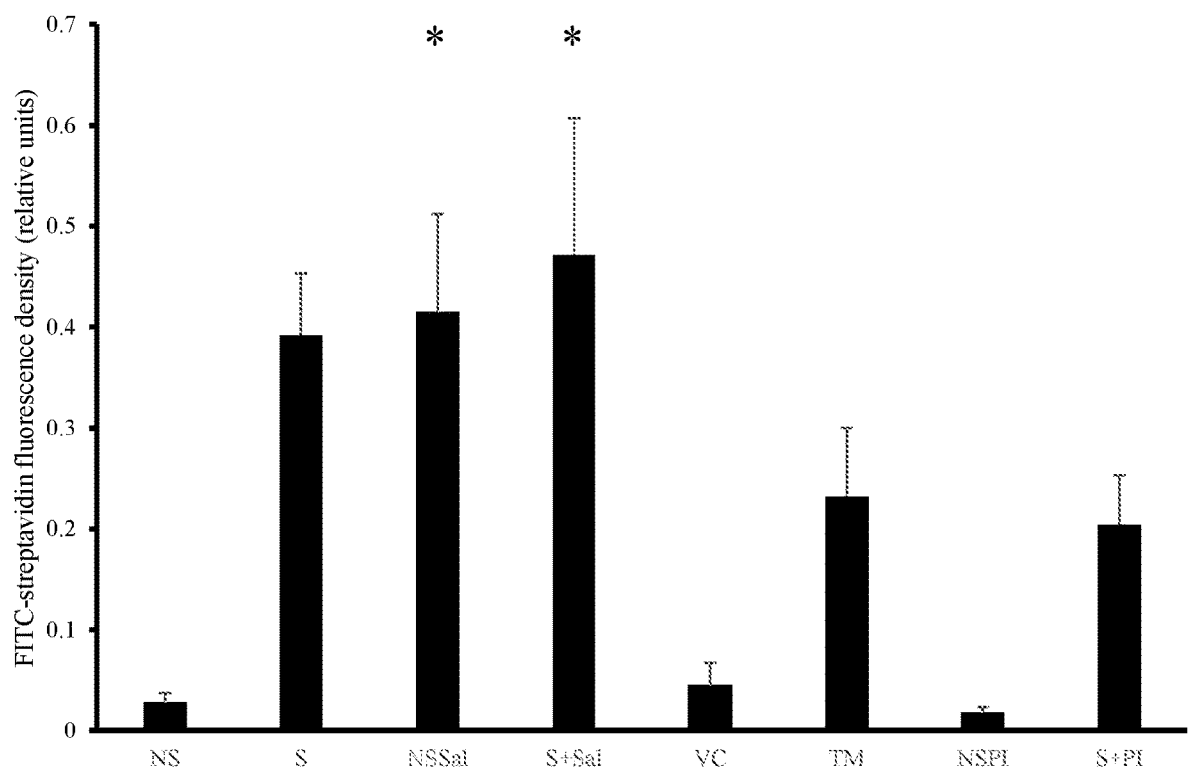
FIG. 9 illustrates that PERK pathway inhibition improves mechanical stretch induced epithelial monolayer permeability. NS—no stretch control; S—6 hrs 25% stretch; NSSal-no stretch 10 uM salubrinal 2 hrs pretreatment; S+Sal—6 hrs 25% stretch and 10 uM salubrinal 2 hrs pretreatment; VC—DMSO; TM—1 ug/ml tunicamycin 24 hrs treatment; NSPI—1 uM PERK inhibitor 24 hrs treatment; S+PI—6 hrs 25% stretch and 18 hrs 1 uM PERK inhibitor pretreatment. N=5-8 independent experiments, *P<0.05 NS or VC vs. treatment, # p<0.05 S vs. S+PI, t-test.
Figure 17A:
FIG. 17A-FIG. 17C shows that PERK siRNA inhibition decreases stretch-induced epithelial monolayer permeability.
Figure 17B:
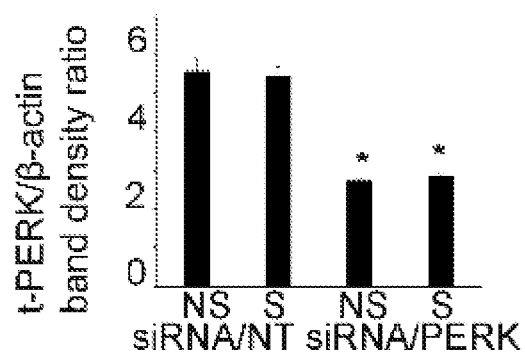
Figure 17C:
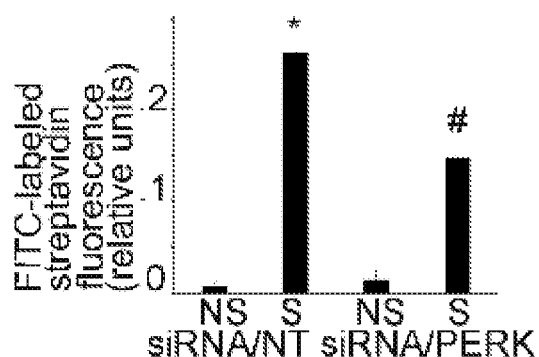

To evaluate whether stretch-induced PERK activation affects epithelial monolayer barrier integrity, monolayers were treated with siRNA specific to PERK and compared results to non-targeting siRNA treatment (FIG. 17A-FIG. 17B). Monolayer integrity was studied with FITC-labeled streptavidin binding to biotin. An intact epithelial monolayer barrier excludes streptavidin from interaction with membrane-bound biotin, but stretch disrupted cell-cell contacts, allowing binding of the two molecules at the basal surface, resulting in quantifiable FITC emission. PERK inhibition improved monolayer dysfunction (FIG. 17C). Monolayer permeability changes in response to stretch were also compared to tunicamycin and salubrinal pretreated monolayers (FIG. 9). Similar to stretch, both tunicamycin and salubrinal treatment resulted in increased permeability.

Figure 3A:
FIG. 3A-FIG. 3G show that PERK phosphorylation inhibition reduces epithelial monolayer dysfunction. AEC-I monolayers were pretreated with 1 µM PERK phosphorylation inhibitor GSK2606414 (PI) or its vehicle 0.01% DMSO for 18 hours before experimentation to evaluate ISR-induced monolayer damage (FIG. 3A). Levels of p-PERK, p-EIF2α, ATF4 and CHOP (FIG. 3A-FIG. 3D, respectively) were unaffected by PI treatment in unstretched monolayers (NS and NSPI). However, PI treatment (SPI) significantly reduced mechanical stretch (S)-induced ISR activation. Quantified densities are shown in FIG. 3B-FIG. 3E.
Figure 3B:
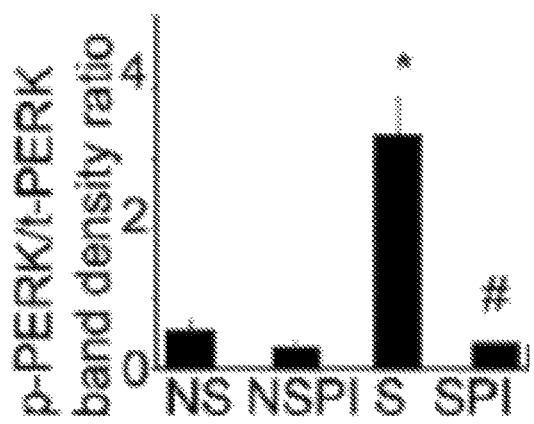
Figure 3C:
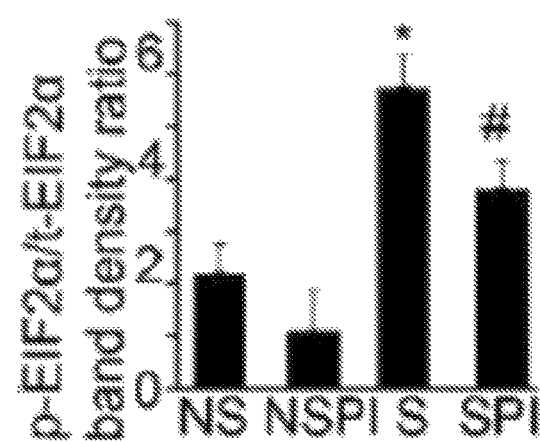
Figure 3D:
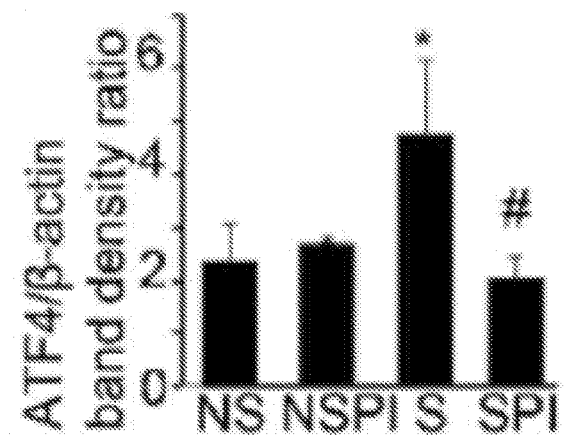
Figure 3E:
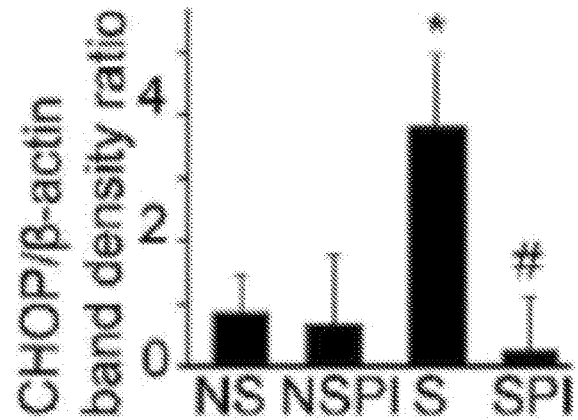
Figure 3F:
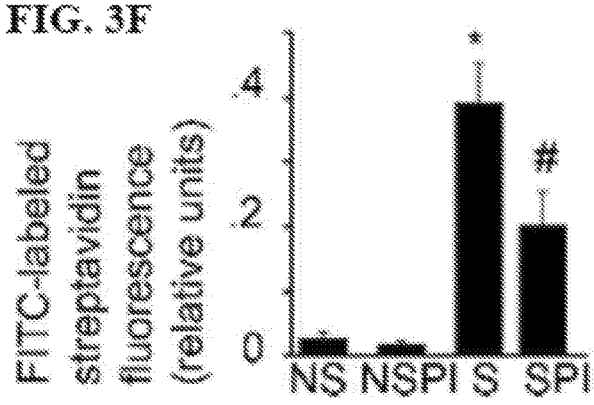
Figure 3G:
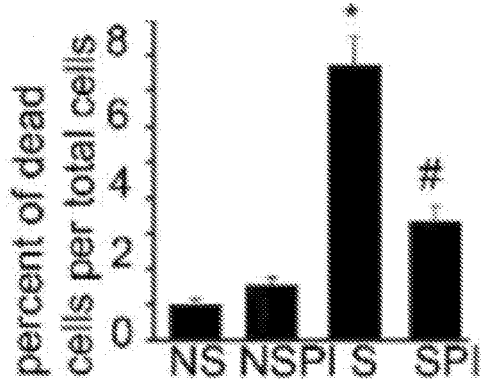
Figure 4A:
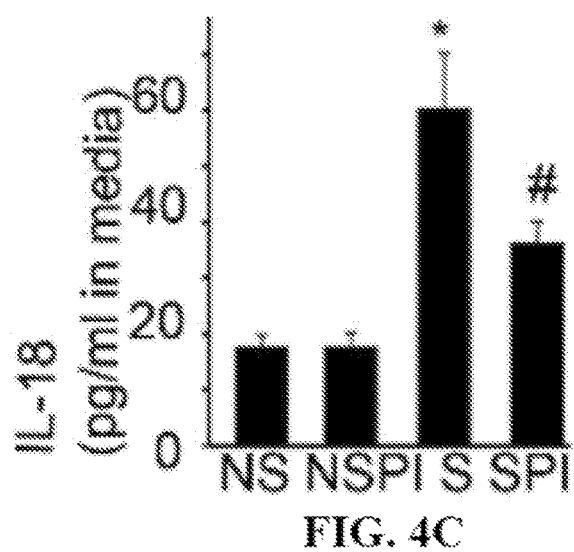
FIG. 4A-FIG. 4G illustrate how ISR regulates epithelial cytokine levels in an IL-18 specific manner.
Figure 4B:
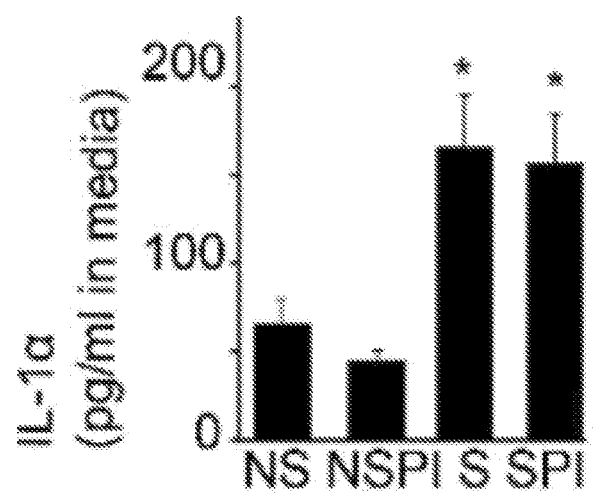
Figure 4C:
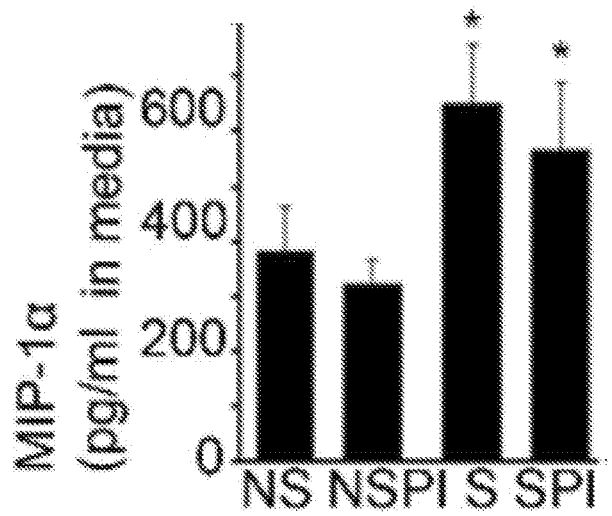
Figure 4D:
Figure 4E:
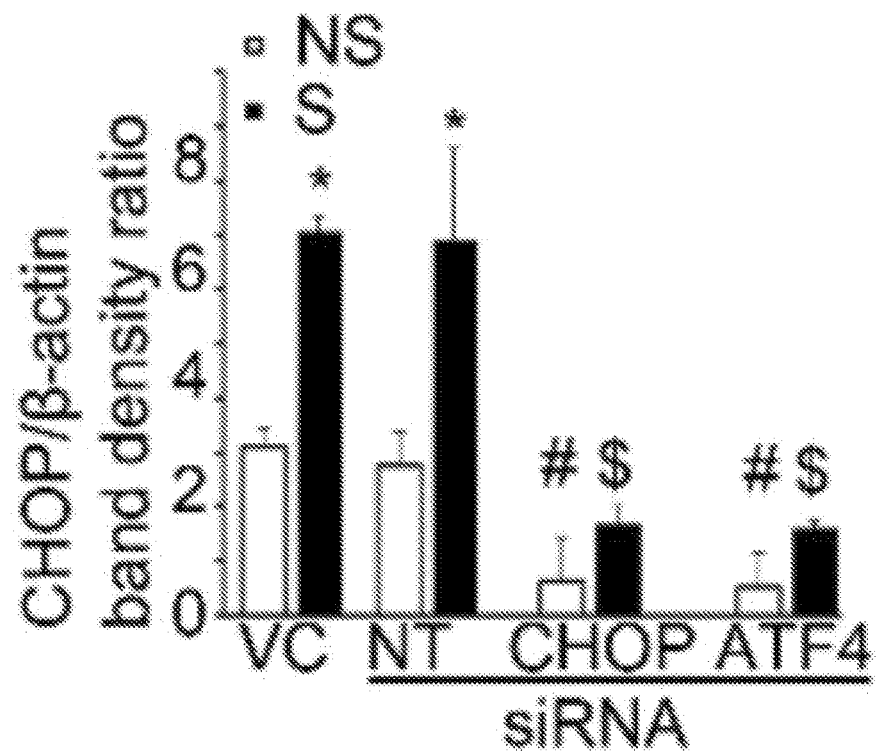
Figure 4F:
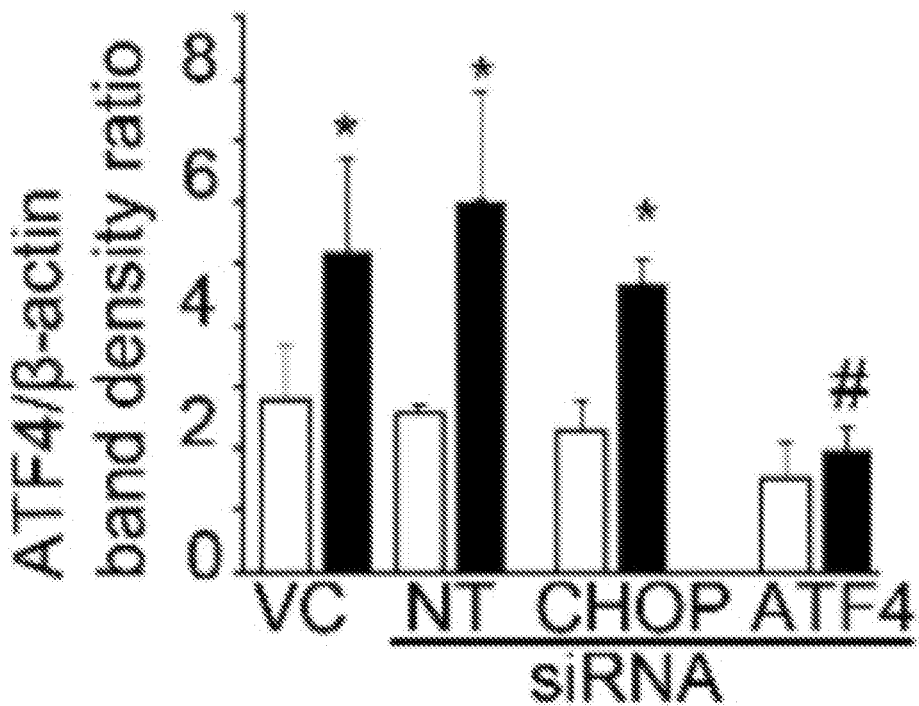
Figure 4G:
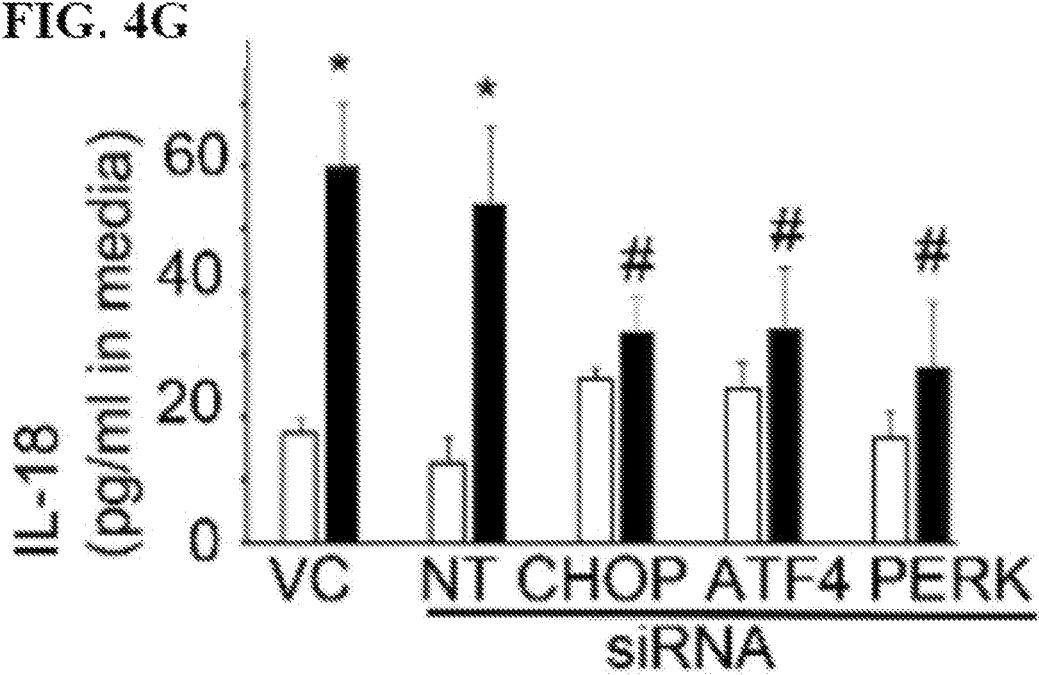
Figure 18:
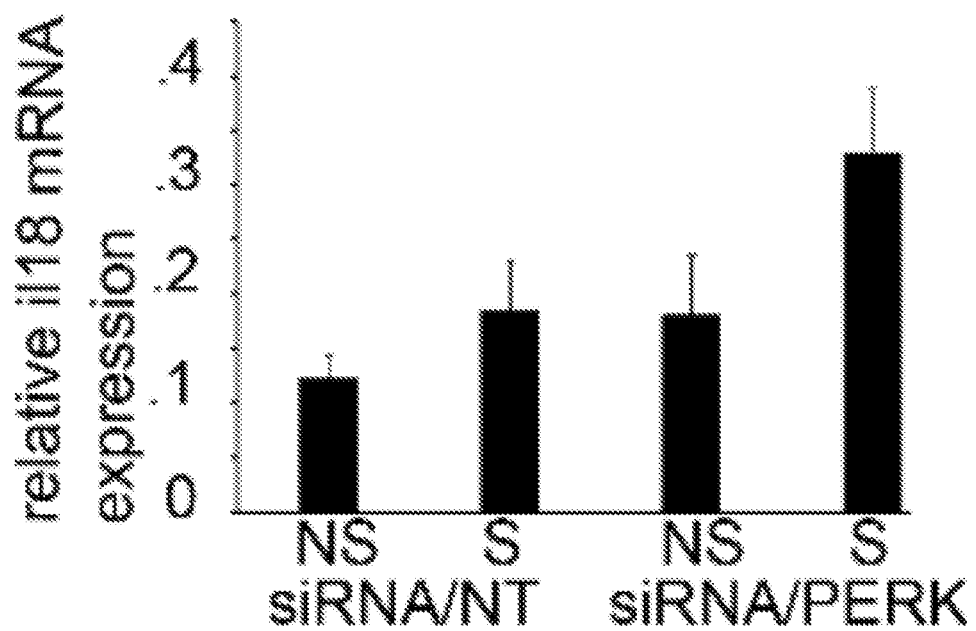
FIG. 18 shows that mechanical stretch and PERK siRNA treatment did not change Il18 gene expression in AEC-I monolayers. TaqMan RT-PCR was performed on total RNA extracted from AEC-I monolayers pretreated for 24 hours with non-targeting (NT) or PERK specific siRNA (PERK). Biaxial cyclic (15/min) mechanical stretch for 6 hours with 25% surface area change did not change il18 RNA expression in the absence or presence of PERK siRNA. N=4 biological replicates/condition.

To evaluate the biological relevance of the observed activation ISR, PERK phosphorylation was chemically inhibited with 1 µM PI (24 hours pretreatment), a major upstream activator EIF2α phosphorylation. PI treatment decreased p-PERK, p-EIF2α, ATF4 and CHOP (FIG. 3A-FIG. 3E) and stretch-induced monolayer permeability, confirming that PERK phosphorylation is critical for ISR-mediated permeability changes (FIG. 3F and FIG. 10B). A decrease in stretch induced cell death was also observed with PI treatment (FIG. 3G), but untreated cell death was low (FIG. 2E). Taken together, the data provides new evidence that alveolar epithelial barrier function is modulated by PERK activation and PI treatment can prevent stretch-induced monolayer barrier damage. Decreased phosphorylation of EIF2α, decreased protein expression of ATF4 and CHOP following PI treatment were observed (FIG. 3A, FIG. 3C-FIG. 3E). Furthermore, PI treatment decreased cell death (FIG. 3G) and differentially affected proinflammatory cytokine levels in the cell culture media. Taken together, this data provides evidence that PERK pathway inhibition as a treatment can mitigate stretch-induced epithelial damage ISR Regulates Epithelial Cytokine Release in an IL-18 Specific Manner Given the interest in cytokines as a biomarker of injury, the contribution of ISR signaling to stretch-induced proinflammatory mediator release was assessed by measuring the level of 26 common cytokines in the culture media in the presence and absence of PI. Generally low cytokine response to stretch was found with modest elevations in IL-18, IL-1α and MIP-1α (FIG. 4A-FIG. 4C). PI treatment decreased IL-18 levels only. (FIG. 4A). To study the regulation of IL-18 by ISR, stretched and unstretched cells were treated with CHOP, ATF4 and PERK siRNA (FIG. 17A-FIG. 17B and FIG. 4D-FIG. 4F). ATF4 siRNA knockdown decreased both ATF4 and CHOP protein expression but CHOP siRNA treatment did not affect ATF4 protein levels confirming that ATF4 is the activator of CHOP signaling in epithelial cells (FIG. 4D-FIG. 4F). Cell culture media IL-18 levels were compared to no siRNA and non-targeting siRNA treatments. It was found that ISR inhibition reduced released IL-18 levels (FIG. 4G), but PERK siRNA treatment, did not affect Il18 mRNA transcription (FIG. 18). Based on these data, it is concluded that ISR regulates the posttranscriptional modification of IL-18 in the alveolar epithelium The Effect of SR Pathway Inhibition on Stretch-Induced RAEC-I Monolayer Permeability To obtain monolayer rat type-II alveolar epithelial cells (AEC-II), cells were isolated from Sprague-Dawley rats (250-300 g, N=30 purchased from Charles River Laboratories, Wilmington, Mass.) described by Tschumperlin D J, Margulies SS. Equibiaxial deformation-induced injury of alveolar epithelial cells in vitro. *Am J Physiol*. 1998; 275(6 Pt 1):L1173-83. Epub 1998/12/09 (PubMed PMID: 9843855), with modifications. Briefly, animals were killed and the lungs were harvested. The lung tissue was digested with elastase at 37° C. and distal airways were isolated. Following, cells were placed on rat IgG coated containing no serum for 90 minutes to eliminate contaminating leukocytes and parenchymal cells. This isolation method yielded approximately 95% pure alveolar epithelial cell population. 1.3 million cells were plated on 1 cm diameter fibronectin-coated custom made silastic membranes. In permeability studies, biotin were mixed with fibronectin and membranes were pretreated with oxygen plasma coating to ensure homogenous distribution of the fibronectin. Cells were cultured with 10% fetal bovine serum (FBS)-containing Minimal Essential Medium (MEM) containing low dose antibiotics for 3 days. 32 to 40 monolayers were per rat. On the 3rd day, matured monolayers were randomized to be exposed to one of the treatments for 24 hours (N=3 monolayers/treatment):

A. RNAiMax transfection reagent treatment using serum free media (Opti-MEM, Thermo Fisher Scientific, Waltham, Mass.). This is a negative control for siRNA experiments where serum free media is used for improved transfection efficiency;
B. non-targeting siRNA treatment (0.5 g/monolayer, Dharmacon) serves a negative control for transfection;
C. 0.5 µg siRNA treatment targeting PERK;
D. 0.5 µg siRNA treatment targeting ATF4;
E. 0.5 µg siRNA treatment targeting CHOP;
F. vehicle control (DMSO) for PI; and
G. 1 µM PI treatment.

The dose of siRNA and PI treatment was selected based on dose-response curves above (FIG. 2A-FIG. 2E). AEC-II transformed to AEC-I cells and formed a complete monolayer by day 4, expressing only AEC-I cell surface markers. On the day of the experiment, the medium was removed and replaced with HEPES-buffered MEM. Cells stretch was performed in a 37° C. incubator. The effect of ISR inhibition or control treatment was compared in the following three conditions (N=5 biological replicates/condition): 1) no stretch (NS) controls; 2) mechanical stretch with 12% surface change (S 12%); and 3) mechanical stretch with 25% surface change (S25%). The cell monolayers were exposed to the above mentioned conditions for 6 hours based on time course of ISR protein expression obtained during preliminary data collection (FIG. 2A-FIG. 2E). All membranes were treated with FITC-labeled streptavidin (Thermo Fisher Scientific) at the end of the experiment and light emission was detected at 488 nm with fluorescent microscopy (Nikon TE300, Melville, N.Y.). In a separate set of experiments (N=30 rats), in which the above mentioned treatment plan and conditions were used, cells were harvested at the end of the experiment by scraping them in RIPA buffer and total protein was extracted (N=3 membranes/treatment group performed for N=5 biological replicates per condition). Co-immunoprecipitation (IP) assays were performed using 5 µg of ZO-1 protein as bait (IP kit, Thermo Fisher Scientific). Following co-IP, immunoblotting was performed for ZO-1, OCLN and CLDN proteins 4, 7 and 18 (Invitrogen, Carlsbad, Calif.).

ISR Pathway Activation and Cell Death in Mechanical Stretch

To assess the effect of ISR inhibition on stretch-induced cell death, dead to live cell ratio was quantified with triple Ethidium homodimer (dead cells)-Calcinein (live cells) and nuclear (DAPI) stain (Thermo Fisher Scientific). Fluorescent light emission from cells was captured with fluorescent microscopy and quantified in the same fashion as described in the "Mechanical stretch activates ISR and cell death in AEC-I" section. N=30 rats were used to obtain data from N=5 biological replicates/condition for each treatment group. Data was expressed as the number of dead cells per total cells as depicted in FIG. 3G. To identify the type of cell death caused by stretch in the model system, additional membranes were stained with cleaved Casp3 (FIG. 7, FIG. 8 and FIG. 10A-FIG. 10B). For these experiments, only the vehicle control treatment and the three stretch conditions will be used (N=5 biological replicates/condition, total N=15 animals).

The preliminary data suggest that there is a differential cytokine response to PI treatment (FIG. 4A-FIG. 4C). Proinflammatory cytokine levels released from alveolar epithelial cells are critical in the initiation of inflammatory response in lung injury. The RNA sequencing data showed that mechanical stretch increased the transcription of key proinflammatory cytokines Interleukin-1β (IL-1β) and macrophage inhibitory protein (MIP-1α) (Table 1) and the secreted levels of IL-18, IL-1α and MIP-1α were also elevated (FIG. 4A-FIG. 4C). Furthermore, PI treatment significantly decreased secreted IL-18 levels. The differential expression of these mediators highlights the interaction between ISR and specific proinflammatory pathways. Based on these findings, the intracellular protein expression and extracellular levels of IL-18, IL-1α and MIP-1α following ISR inhibition will be studied in the future. To gain an overall picture of cytokine response to ISR inhibition in stretch, it is important to measure intracellular protein expression and extracellular levels in parallel because preformed cytokines released cytokine concentration may not reflect production rather than loss of cell integrity. This is further emphasized by the fact that mechanical stretch and PI treatment only affected IL-18 protein levels but no mRNA expression FIG. 4A and FIG. 18. Protein will be extracted from monolayers exposed to each treatment with and without stretch and cell culture supernatant will be for further analysis. Released cytokine levels will be will be measured with ELISA (R&D Systems, Minneapolis, Minn.) and intracellular protein expression will be measured with western immunoblotting. Rat specific IL-18, IL-1α and MIP-1α antibodies are available from Santa Cruz Biotechnologies (Santa Cruz, Calif.). N=30 animals will be used for these experiments. Protein expression will be quantified using densitometry.

To gain sufficient statistical power to detect significant differences across treatment modalities and stretch conditions, 3 monolayers/treatment groups and data gathered from N=5 animals were used for each stretch modality. Based on the preliminary data with these sample numbers, a 20% change with a <5% error rate (p<0.05) can be detected to test for significance. To control for animals, animals of the same age (approximately 1 month old) were obtained from the same vendor (Charles River Laboratories). While there is no scientific evidence rodent epithelial cells have a gender specific response to injury, both genders were included in the studies because women have been shown to be at increased risk for ARDS.

Photomicrographs of 3 independent areas of each monolayers will be taken and the intensity of light emission will be quantified comparing values to maximum pixel density of the background using custom designed software (Mat lab, Math works, Natick, Mass.) modified after Song et al., Local influence of cell viability on stretch-induced permeability of alveolar epithelial cell monolayers, *Cellular and molecular bioengineering* 2016; 9(1):65-72. Briefly, the maximum pixel intensity in the background of upstretched-untreated monolayers will be measured and used as a threshold to exclude unstained regions. The percentage of each image area (3 images/well, 3 wells/animal, from 5 animals/group) above the threshold intensity will be determined and then divided by the respective value for the unstretched-vehicle control group to calculate the normalized area percentage (area) of each image. To test the effect of a stretch condition, n Area values will be compared with time-matched upstretched-control values using a one-way ANOVA with post hoc Dennett's test in JMP (SAS Institute, Cary, N.C.). To test the effect of inhibitor treatment, animal average n Area values will be compared with vehicle controls, as well as unstretched-untreated controls, using a two-way ANOVA with Tukey-Kramer post hoc analysis in JMP. Data will be expressed as mean and standard error of mean (±SEM)

Immunoblot protein expression of OCLN and CLDN was quantified using densitometry and normalized to ZO-1 (ImageJ, NIH, Bethesda, Md.). IL18, MIP-1α and IL-6 protein expression was normalized to B-actin. In ELISA, cytokine levels will be expressed in relation to standard protein dilution curves provided by the vendor. Data will be compared in each treatment group among stretch conditions. Kruskal-Wallis test will be used for multiple group comparison, and intergroup differences will be analyzed with the Wilcoxon rank sum test using SAS.

ISR Activation by Mechanical Ventilation in Lung Tissue

Figure 11A:
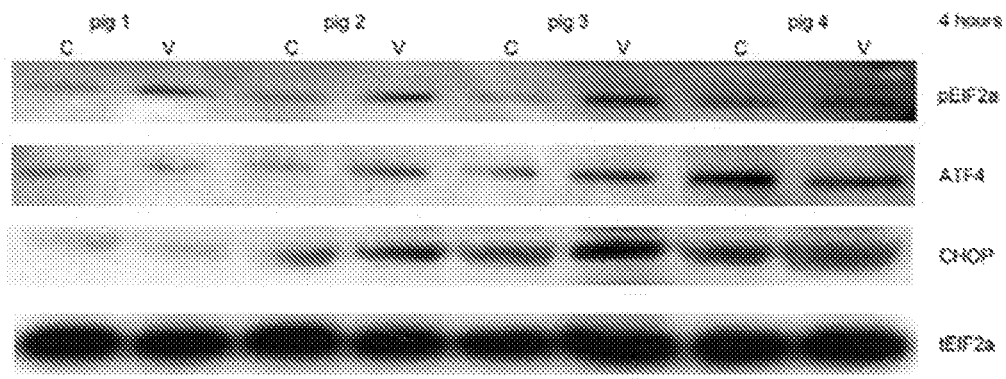
-FIG. 11D illustrates that mechanical ventilation activates the ISR response in pig lung tissue ex vivo. N=4 independent experiments. *P<0.05 control vs. ventilation, Kruskal-Wallis test.
Figure 11B:
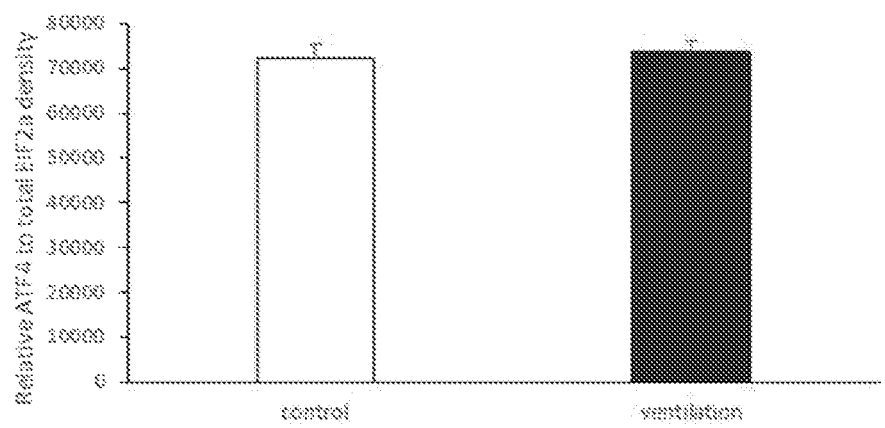
Figure 11C:
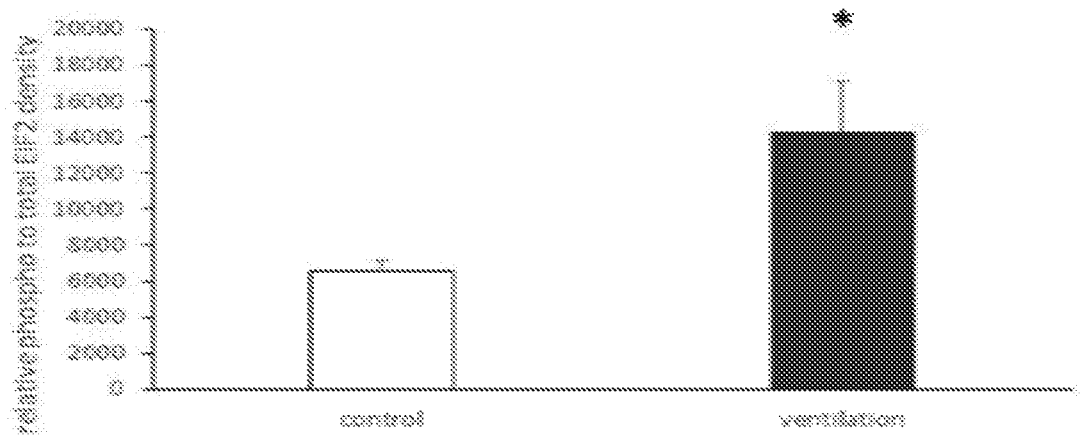
Figure 11D:
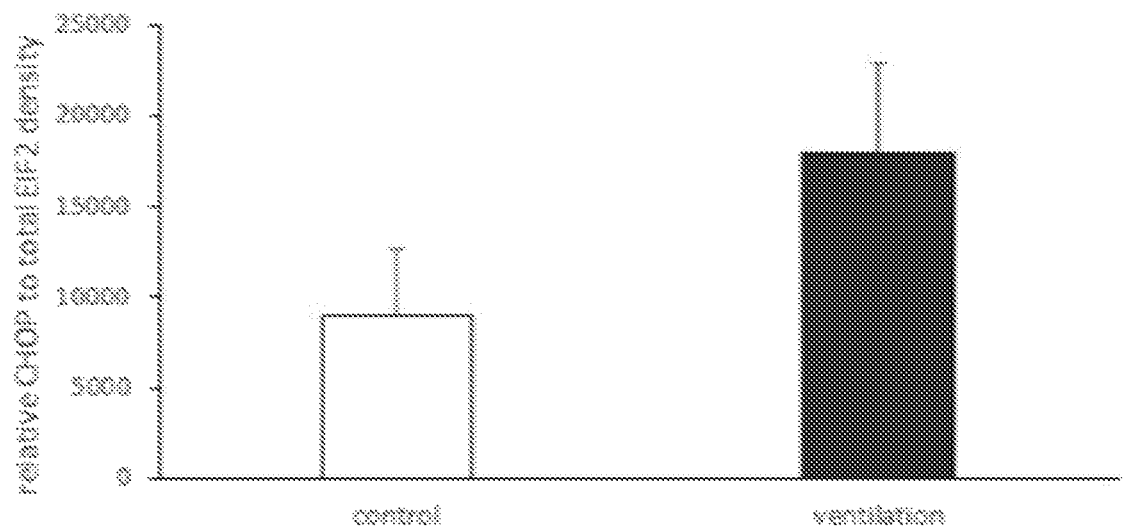

The effect of high alveolar pressure on ISR signaling was tested in an ex vivo perfused and ventilated pig lung tissue. Pig lung and heart complexes were perfused with 3% fetal bovine serum containing minimal essential medium via the pulmonary artery and mechanically ventilated via the trachea for 4 hours with 30 cmH2O pressure (V), corresponding to approximately 12 ml/kg tidal volume with no positive end expiratory pressure (PEEP). This mechanical ventilation is considered injurious resulting in VILI in live animals. The left middle lobe (pig lobe) airway was tied off and served as a perfused but not ventilated lung lobe (C). Total protein was extracted from the right lower lobe and the pig lobe. Western blot analysis was performed for t- and p-EIF2α, ATF4, CHOP (FIG. 11A). FIG. 11B-FIG. 11D. Quantified data show significant increase in p-EIF2α following ventilation when compared to controls. While expression increased in ATF4 and CHOP as well it did not reach significance. *represents significant increase, p<0.05, Kruskal-Wallis test, N=4/group.

Figures 12A, 12B:
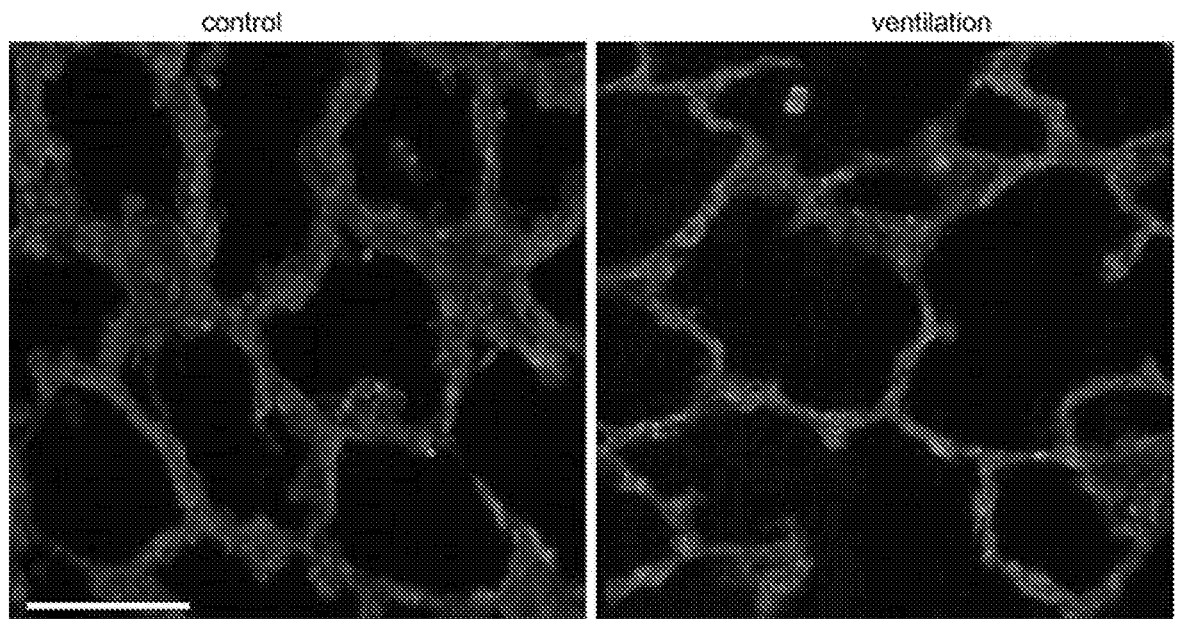
FIG. 12A-FIG. 12B illustrates pig lung tissue 4 hours ex vivo ventilation with 30 cmH$_2$O pressure.

The expression of p-EIF2α was also compared between ventilated and control pig lung tissues with immunofluorescent staining (FIG. 12). Light emission was detected with fluorescent microscopy (Nikon TE300, Melville, N.Y.). Increased fluorescence of Alexa fluor 488 nm (green) labeled antibody against p-EIF2α was observed in ventilated tissue (ventilation) when compared to non-ventilated preparations. Representative slides of the two conditions are shown. To confirm that mechanical ventilation increases EIF2α phosphorylation in alveolar epithelial cells, we co-stained the slides with Alexa-594 nm (red) labeled occludin, which is an epithelial cell marker (FIG. 12). Phosphorylated EIF2α was present in occluding positive cells suggesting that mechanical ventilation increases EIF2α phosphorylation in the epithelium as well as in other alveolar cell types.

Figure 20A:
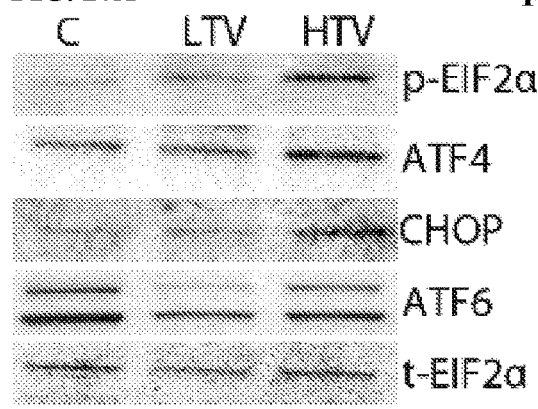
FIG. 20A and FIG. 20B illustrate how mechanical ventilation activates integrated stress response in a tidal volume dependent fashion in an ex vivo porcine model of mechanical ventilation. Lung and heart complexes were removed from pigs (Yorkshire, 8-10 kgs) post euthanasia. The main pulmonary artery was cannulated and connected to a peristaltic pump and the lungs were continuously perfused with 1% albumin containing MEM tissue culture media. Lung tissue was ventilated for 4 hours with low (6 ml/kg, LTV) or high (12 ml/kg, HTV) tidal volume mechanical ventilation. Non-ventilated but perfused left middle lobe (pig lobe) lung tissue served as controls (C). Western blot analysis was performed on whole lung tissue protein for p- and t-EIF2α, ATF4, CHOP and ATF6 (FIG. 20A). Quantified data show significant increase in p-EIF2α following HTV but not LTV when compared to C (FIG. 20B). Protein expression changes in ATF4, 6 and CHOP were not significant. *represents significant increase, p<0.05, Kruskal-Wallis test, N=4 complexes/group. Abbreviations: p- and t-EIF2α=phospho- and total-eukaryotic initiation factor 2a, ATF4 and ATF6=activation transcription factor 4 and 6, CHOP=CCAAT/enhancer-binding protein homologous protein.
Figure 20B:
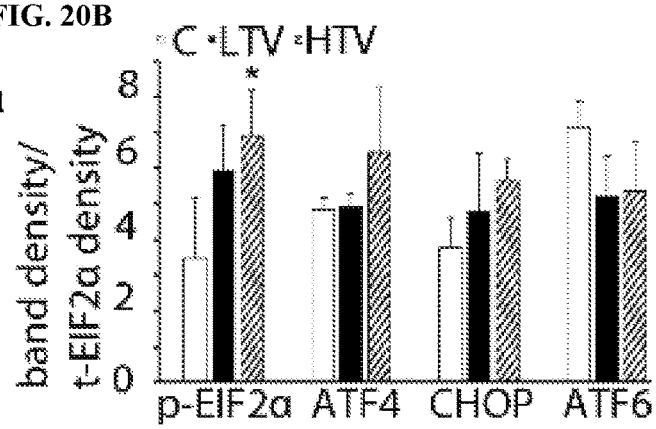
Figure 21A:
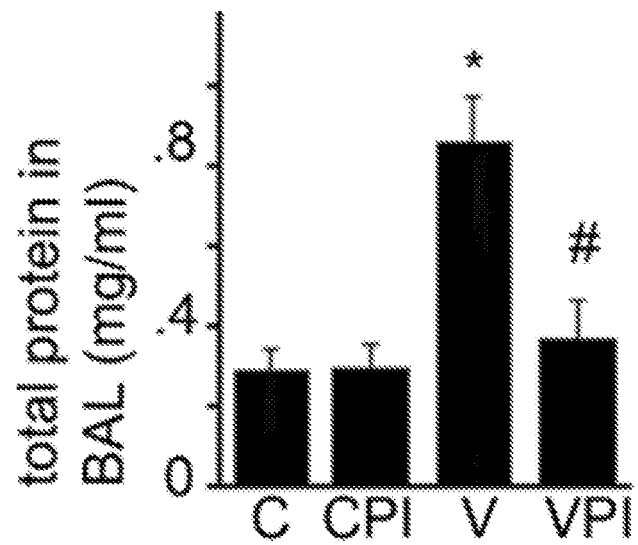
FIG. 21A-FIG. 21G exemplifies how oral PERK inhibitor pre-treatment can mitigate VILI. Lung injury indices were compared between spontaneously breathing (C) and ventilated (V, 20 mg/kg, 4 hrs) rats (Sprague-Dawley, 250-300 grs) in the absence or presence of PERK inhibitor (PI). Ventilation-induced BAL total protein content (FIG. 21A) and lung injury score (FIG. 21B) significantly reduced in the presence of 30 mg/kg PI. Dose titration experiments (3-30 mg/kg) showed that 10 mg/kg PI may be sufficient to reduce alveolocapillary permeability (FIG. 21C), total BAL cell count (FIG. 21D) neutrophil count (FIG. 21E) and IL-18 cytokine levels (FIG. 21F). PI treatment did not reduce serum IL-18 levels (FIG. 21G). * represents significant increase between C and V conditions. # represents significant decrease between V and VPI conditions. P<0.05, Kruskal-Wallis Test, N=5-9 animals/group.
Figure 21B:
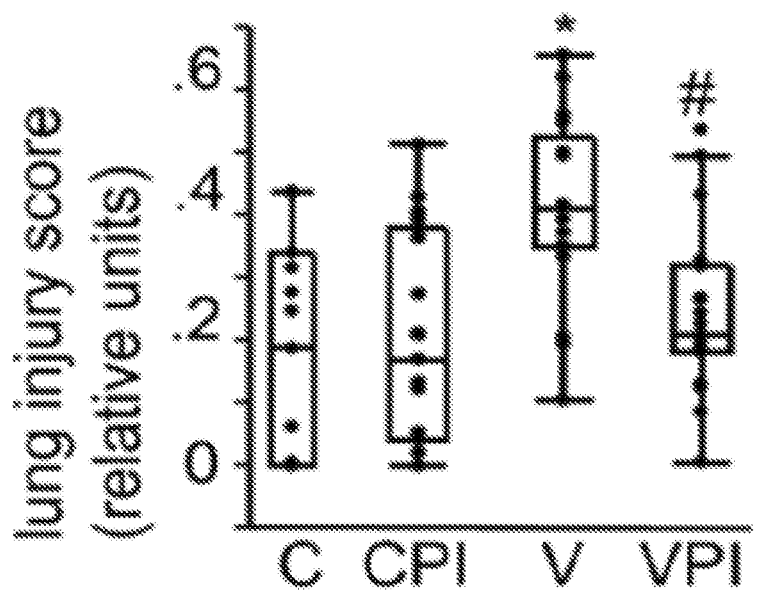
Figure 21C:
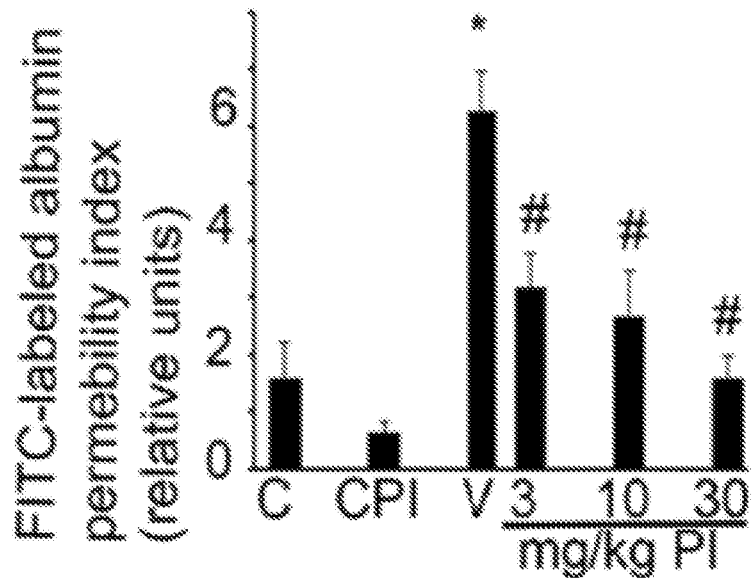
Figure 21D:
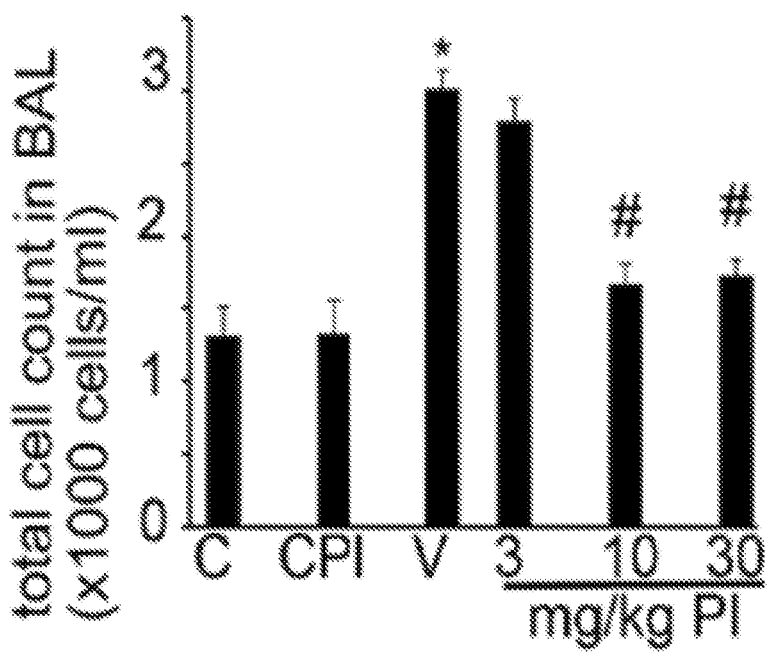
Figure 21E:
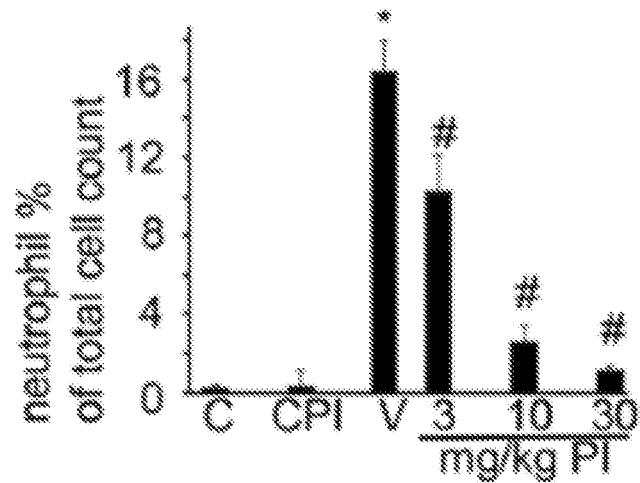
Figure 21F:
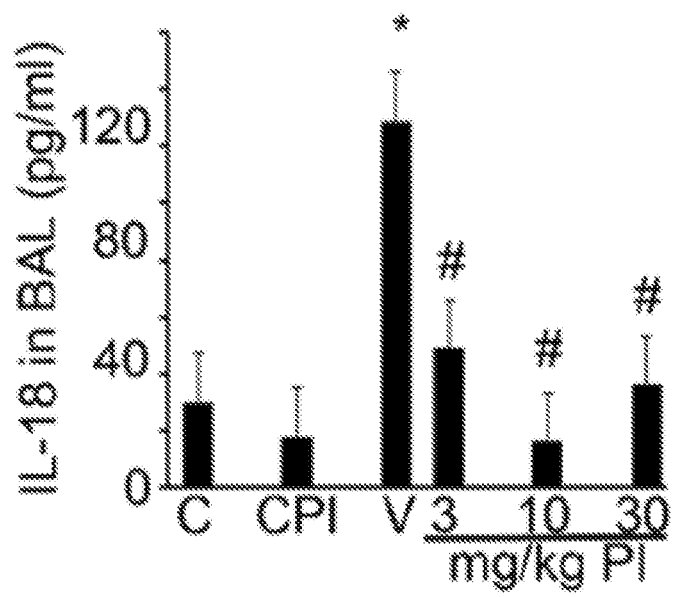
Figure 21G:
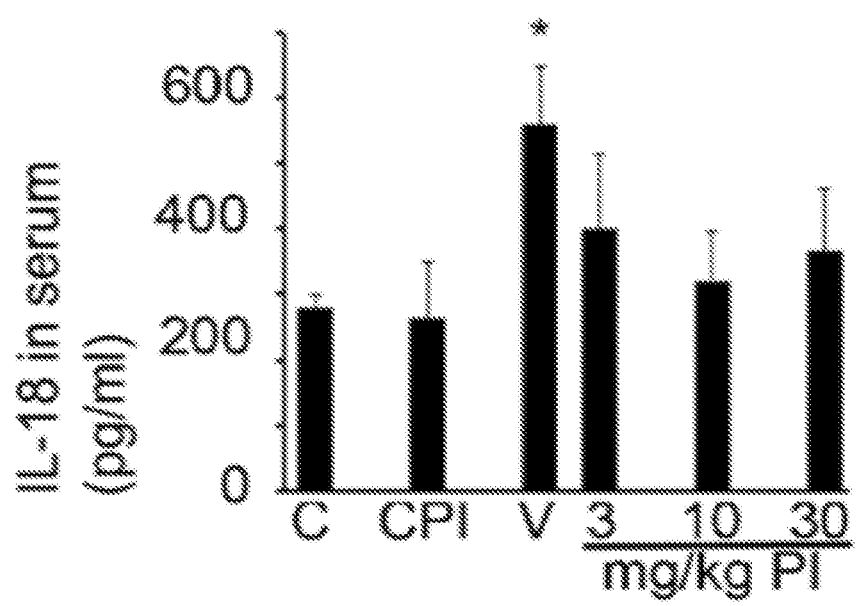
Figure 22A:
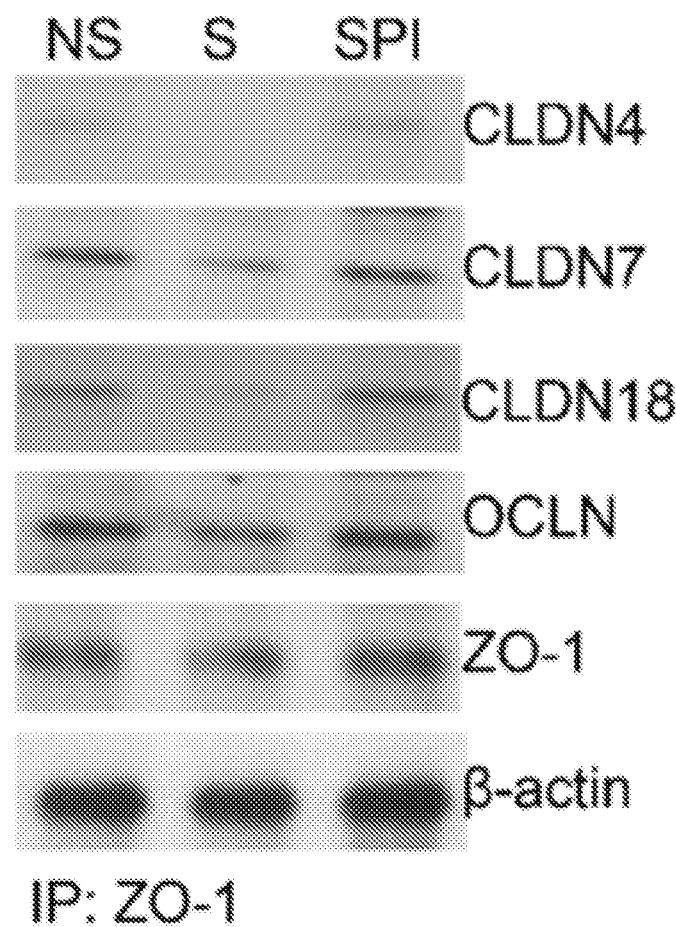
FIG. 22A-FIG. 22E exemplifies how PERK inhibition can prevent stretch-induced tight junction protein dysfunction in alveolar epithelial cell monolayers. Rat primary type-I like alveolar epithelial cell (AEC-I) monolayers were exposed to mechanical cyclic stretch (25% surface change for 6 hours, 15/min frequency, S) and the expression of specific epithelial tight junction (TJ) proteins was compared to unstretched (NS) monolayers (FIG. 22A). Co-immunoprecipitation was performed from total cellular protein for claudin (CLDN) 4,7,18 and occludin (OCLN) using zonula occludens (ZO)-1 as bait. Mechanical stretch resulted in the dissociation of tight junction (TJ) proteins from zonula occludens (ZO)-1, which caused epithelial monolayer dysfunction. PERK inhibitor pretreatment of stretched monolayers (SPI) prevented stretched-induced TJ protein dissociation.
Figure 22B:
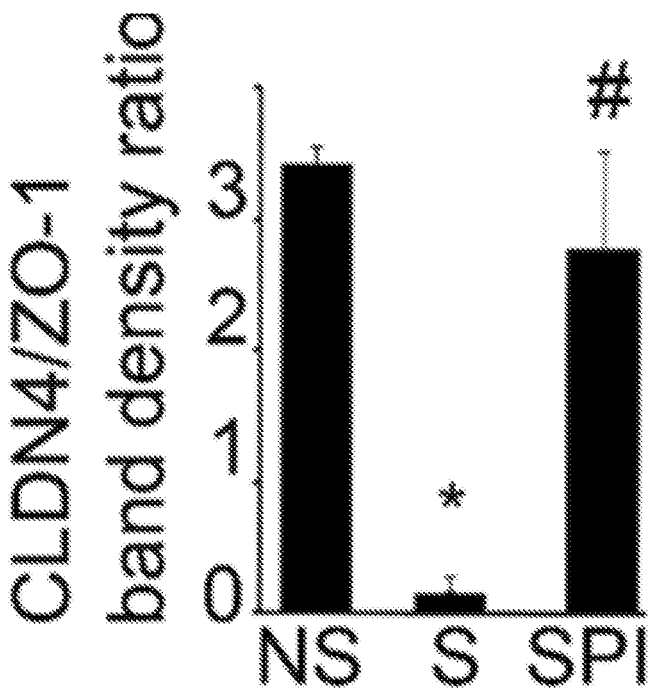
Figure 22C:
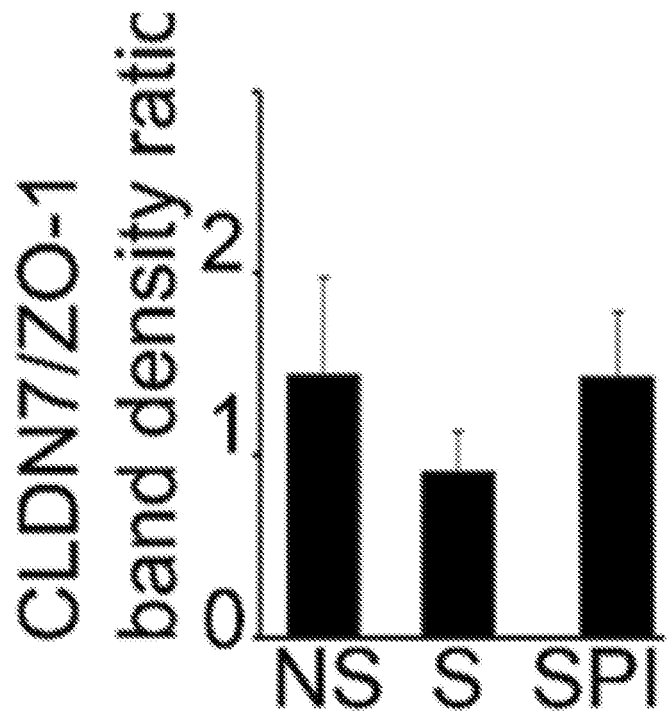
Figure 22D:
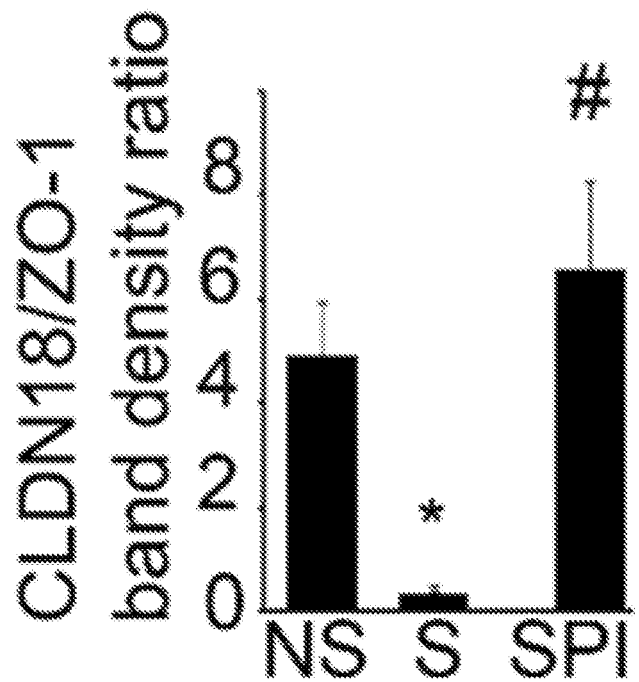
Figure 22E:
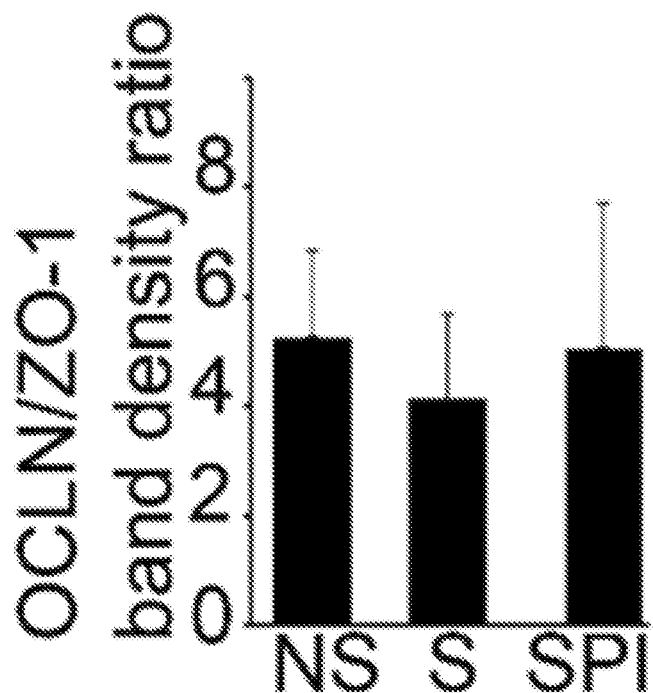

Low tidal volume (LTV) mechanical ventilation (less 6 mg/kg tidal volume adjusted to ideal body weight) is the standard of care for patients with acute lung injury and ARDS. We compared LTV to high tidal volume (12 ml/kg, HTV) and no ventilation (C) conditions in ex vivo ventilated pig-lungs and found that LTV did not significantly activate ISR (FIG. 20A-FIG. 20B). HTV significantly increased p-EIF2α and borderline elevation in ATF4 and CHOP expression. ATF6 levels did not change with either ventilation protocols. Quantified data is shown in FIG. 20B.

Figure 5:
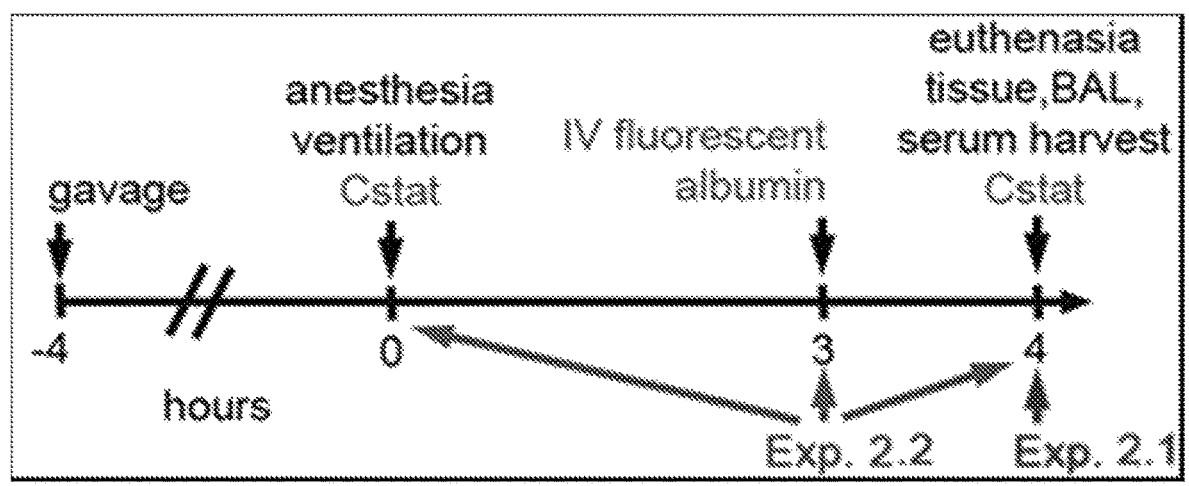
FIG. 5 illustrates that PERK inhibitor (PI) treatment plan in rat ventilator-induced lung injury (VILI). Black font represents procedures for both Experiment 1 and 2, gray font represents procedures for Experiment 2. Cstat=static lung compliance.

In Vivo Validation of the Therapeutic Effectiveness of Concurrent ISR Pathway Inhibition in VILI Animal VILI experimental models represent a widely accepted and sophisticated tool for translational research in which basic biology studies in vitro can be coupled with physiology measurements. A schematic presentation these experiments are shown in FIG. 5. Adult male Sprague-Dawley rats (N=174, weight 250-300 g) were purchased from Charles River Laboratories (Horsham, Pa.). Rats were allowed to acclimate for 1 week with rodent chow and water ad libitum.

Figure 13:
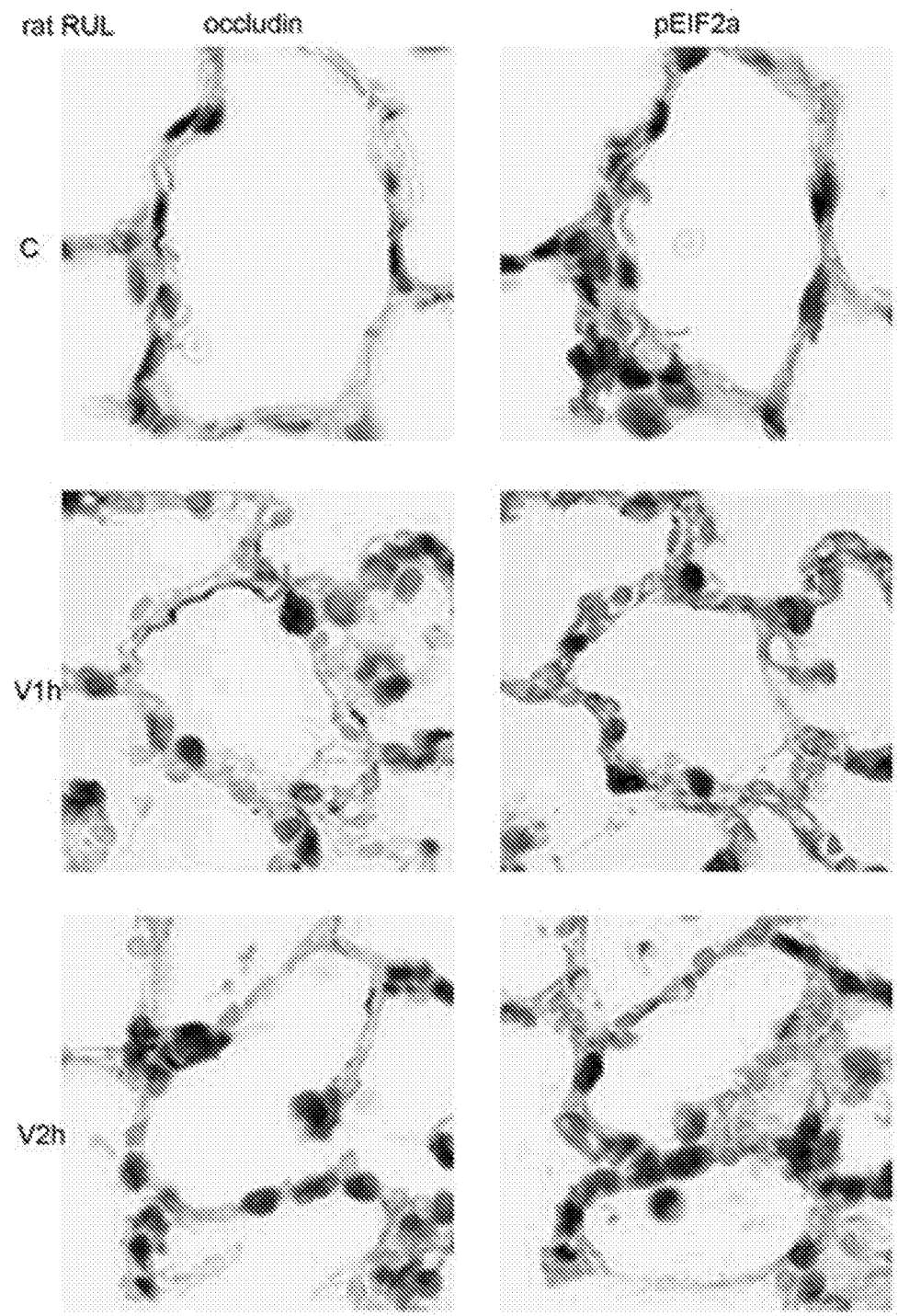
FIG. 13 illustrates rat in vivo mechanical ventilation with 20 ml/kg tidal volume and no PEEP. Mechanical ventilation for 1 (V1h) and 2 hours (V2h) increases EIF2a phosphorylation in alveolar epithelial cells when compared to non-ventilated tissue (C).

To establish the feasibility of translating the in vitro findings to in vivo, a rat model of VILI was used. Animals were pretreated via oral gavage with either 30 mg/kg PI or its vehicle for 4 hours prior to the start of the experiment. Rats were ventilated with 20 ml/kg tidal volume via tracheostomy for 4 hours without positive end expiratory pressure (PEEP) or a recruitment maneuver to induce injury. The lung tissue of ventilated animals was compared to spontaneously breathing controls. Immunohistochemical analysis of 1 hour (V1h) and 2 hours (V2h) ventilated lung tissue demonstrated increase in EIF2α phosphorylation when compared to non-ventilated control (C) lungs (FIG. 13). Staining for epithelial marker, occludin, suggests that EIF2α phosphorylation is as least in part, localized to the alveolar epithelium. To confirm these findings, immunofluorescence analysis of thin cut sections was performed using a Zeiss LSM 880 laser scanning confocal microscope (FIG. 19). This analysis showed increased EIF2α phosphorylation in response to mechanical ventilation (FIG. 19A-FIG. 19C) in multiple alveolar cell types including type-I alveolar epithelial cells labeled with occludin (FIG. 19D).

Figure 6A:
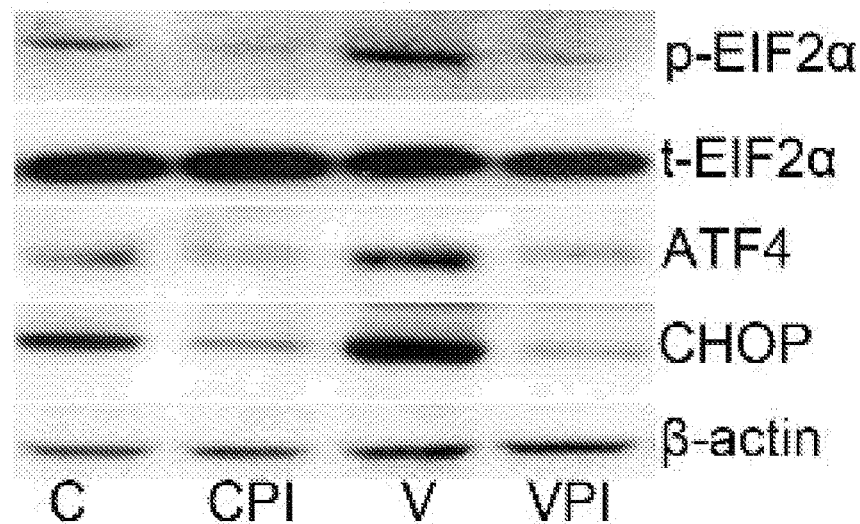
FIG. 6A-FIG. 6K show oral PI treatment reduces ISR activation and improves ventilator-induced lung injury (VILI).
Figure 6B:
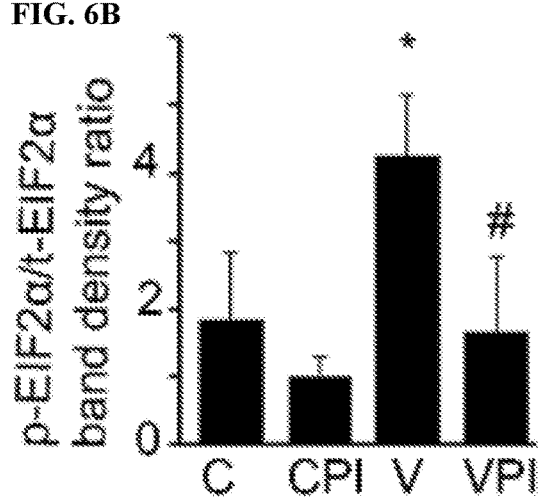
Figure 6C:
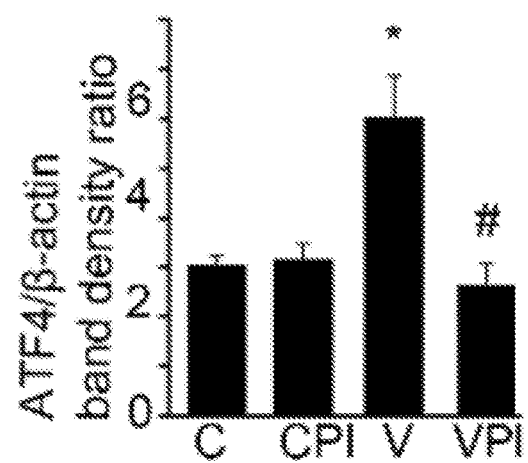
Figure 6D:
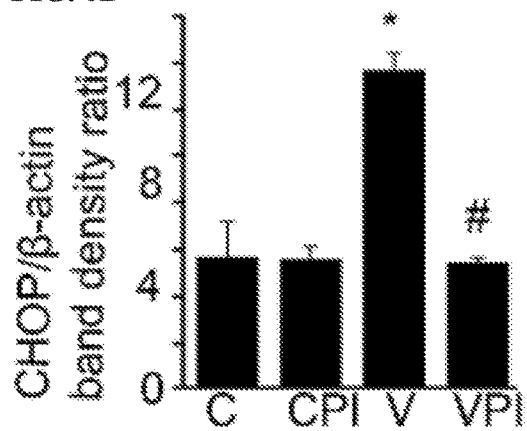
Figure 6E:
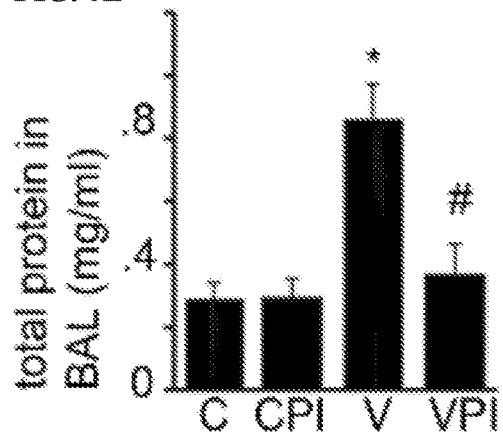
Figure 6F:
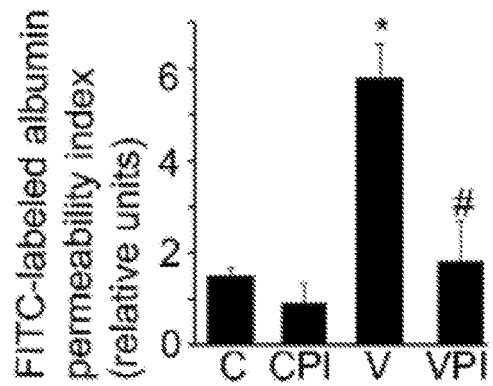
Figure 6G:
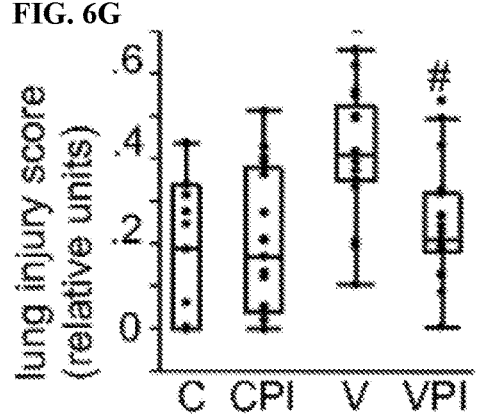
Figure 6H:
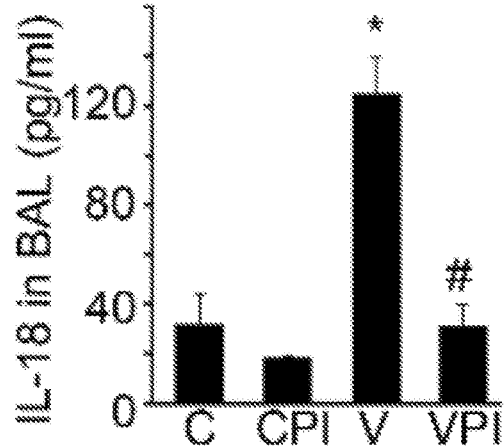
Figure 6I:
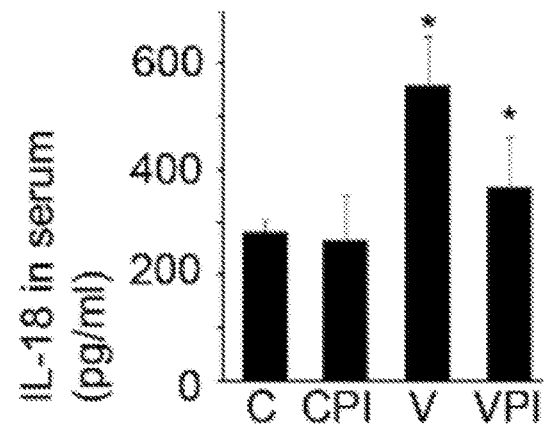
Figure 6J:
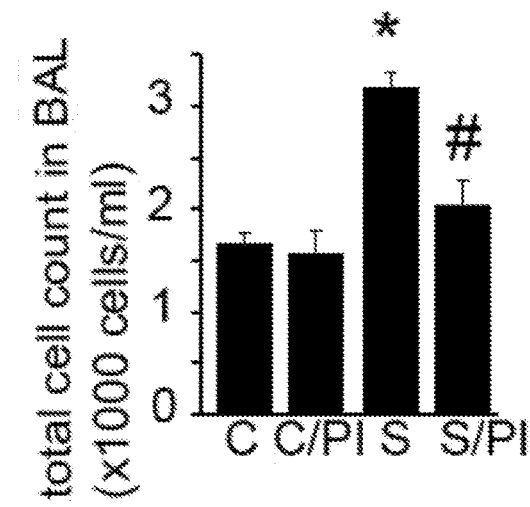
Figure 6K:
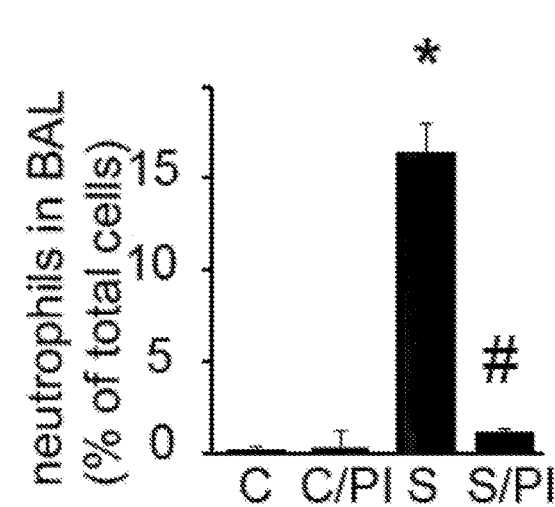
Figure 7A:
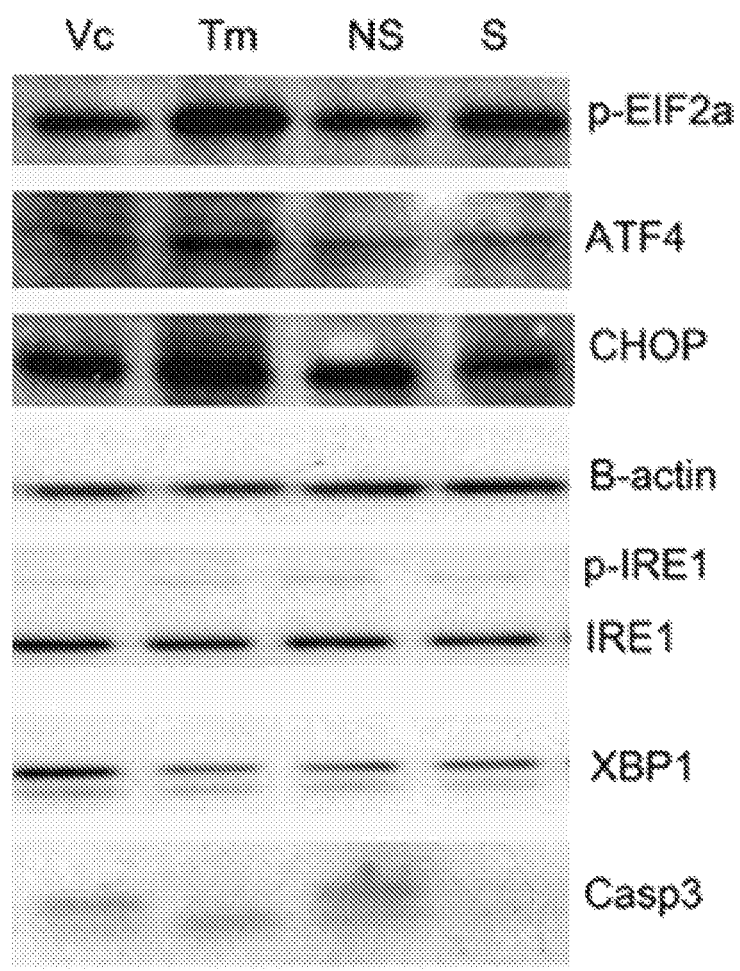
FIG. 7A-FIG. 7E illustrate that ISR activation is independent of IRE1 pathway in mechanical stretch. VC—vehicle control (DMSO for tunicamycin), Tm-1 µg/ml tunicamycin 24 hrs, NS—no stretch control, S—6 hrs 25% mechanical stretch. N=3-5 independent experiments, *p<0.05, S vs. NS, Kruskal-Wallis test.
Figure 7B:
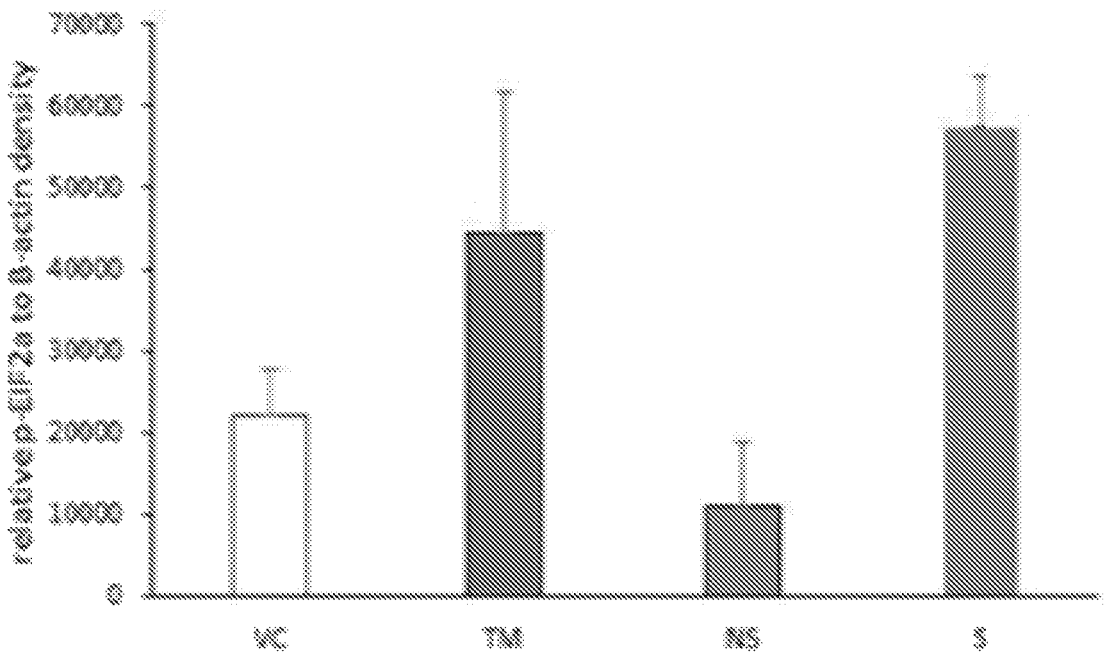
Figure 7C:
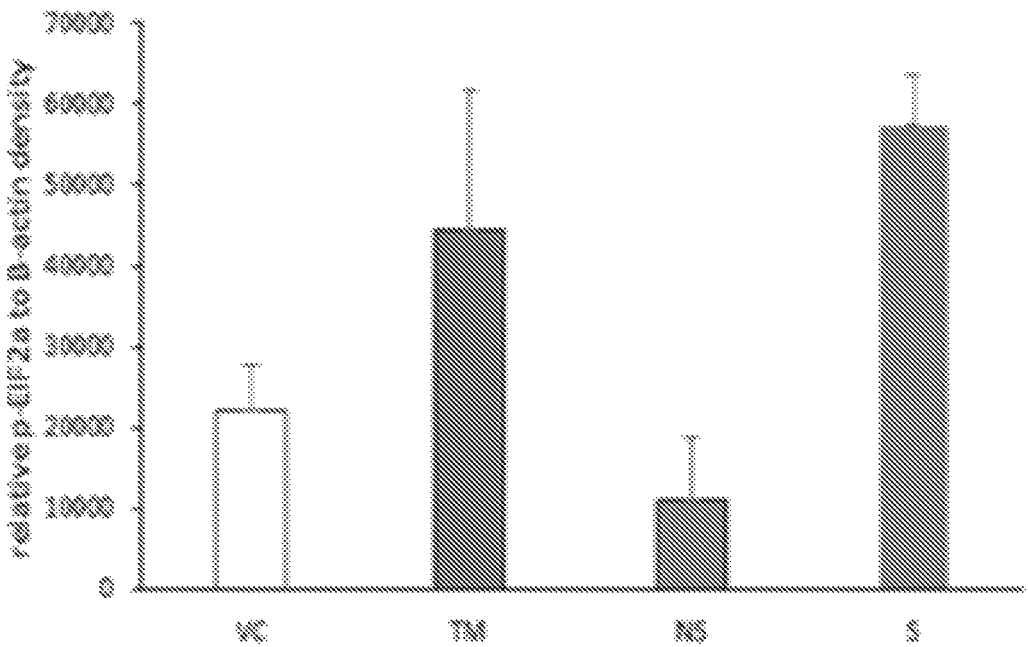
Figure 7D:
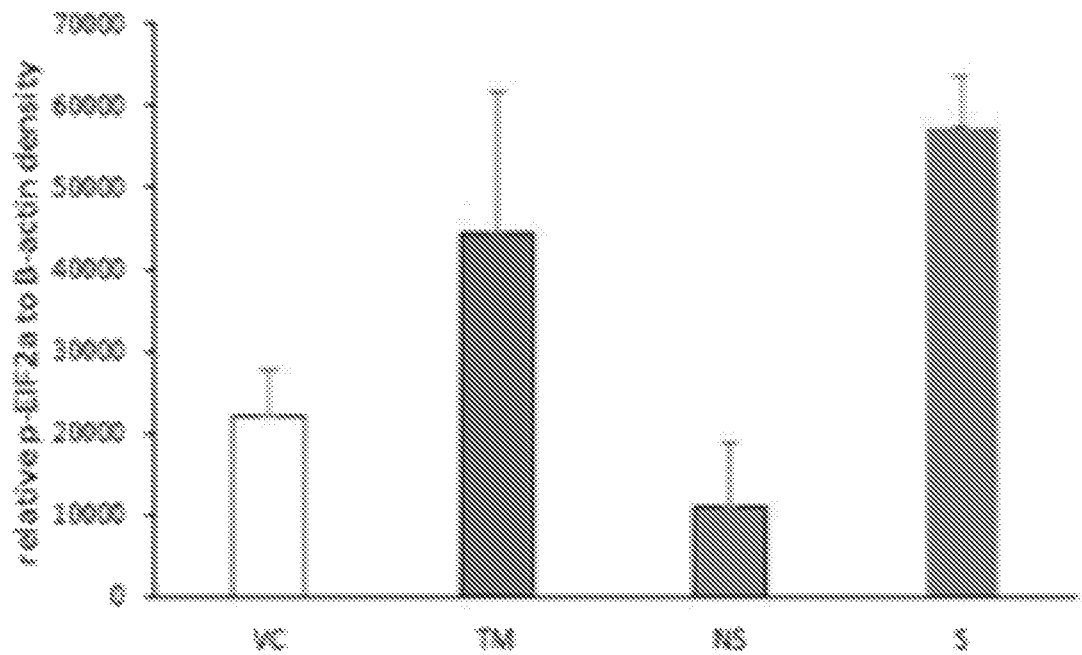
Figure 7E:
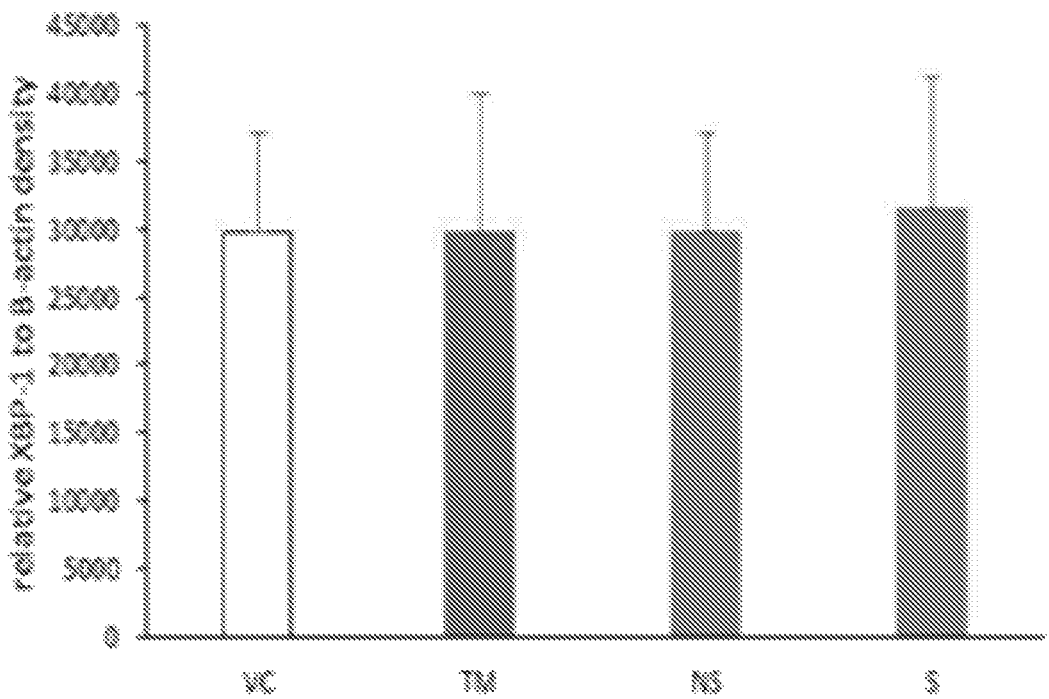

Tissue homogenate results support the in vitro epithelial stretch findings, with ISR activation via increased EIF2α phosphorylation and subsequent activation of ATF4 and CHOP following mechanical ventilation (FIG. 6A-FIG. 6D). PI treatment significantly decreased ISR activation in the lung tissue of ventilated animals compared to vehicle treated ventilated rats (FIG. 6A-FIG. 6D), but PI had no effect on spontaneously breathing animals. These findings suggest that PERK inhibition in vivo can alter ISR signaling. The effect of PERK inhibition on lung injury indices was measured. PERK inhibition significantly decreased bronchoalveolar lavage (BAL) total cell count, neutrophil cell count and total protein content (FIG. 6E, FIG. 6J-FIG. 6K).

Oral PI Treatment Improves VILI

Acute lung injury is characterized by lung inflammation, pulmonary edema and proinflammatory cytokine release. To test whether PI treatment in vivo reduces lung injury, the impact of PI was first measured on bronchoalveolar lavage (BAL) cell count.

TABLE 2

| Condition | Total cell count ($\times 10^3$ cells/ml BAL) | Macrophage cell count ($\times 10^3$ cells/ml BAL) | Neutrophil cell count ($\times 10^3$ cells/ml BAL) |
| --- | --- | --- | --- |
| C   | 1.32 ± 0.18  | 0.56 ± 0.04 | 0.003 ± 0.001 |
| CPI | 1.44 ± 0.23  | 0.77 ± 0.17 | 0.003 ± 0.003 |
| V   | 3.01 ± 0.13* | 1.69 ± 0.23 | 0.48 ± 0.06* |
| VPI | 1.75 ± 0.14* | 1.28 ± 0.26 | 0.03 ± 0.009† |

As depicted in Table 2, mechanical ventilation significantly increased total, macrophage and neutrophil cell count in the bronchoalveolar lavage (BAL) fluid of mechanically ventilated rats. Pretreatment with PERK inhibitor significantly reduced total BAL macrophage count and neutrophil accumulation in the alveolar space. C=control, spontaneously breathing animals, pretreated with drug vehicle (0.1% TWEEN 80 in 0.5% hydroxyethyl-methylcellulose) 4 hours before sacrifice. CPI=control animals pretreated with 30 mg/kg PERK inhibitor GSK2606414 four hours prior to sacrifice, V=vehicle pretreated rats mechanically ventilated for 4 hours with 20 ml/kg tidal volume without positive end expiratory pressure and recruitment maneuver, VPI=mechanically ventilated rats as in condition V, pretreated with 30 mg/kg PI four hours prior to the start of ventilation. *represents significant change in cell count C vs. V condition and †represents significant difference between V and VPI conditions, p<0.05. N=8 animals were used/condition.

Figure 14:
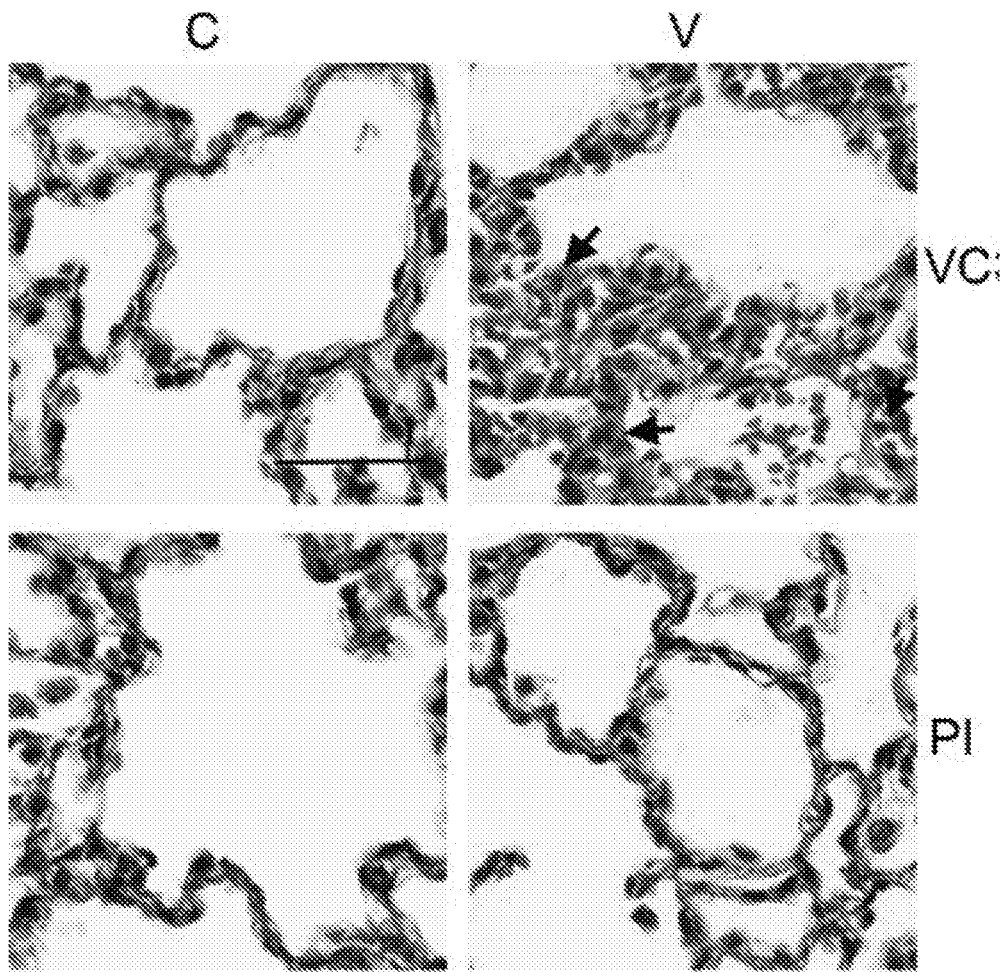
FIG. 14 illustrates that PERK inhibition prevents lung tissue damage in VILI. The effect of drug vehicle (VC) and PERK inhibitor (PI) treatment on lung tissue histology is shown in ventilated (V) and spontaneously breathing control (C) animals. Arrows point at neutrophils infiltrating the alveolar septi. Scale bar=50 µm, H&E staining.
Figure 15:
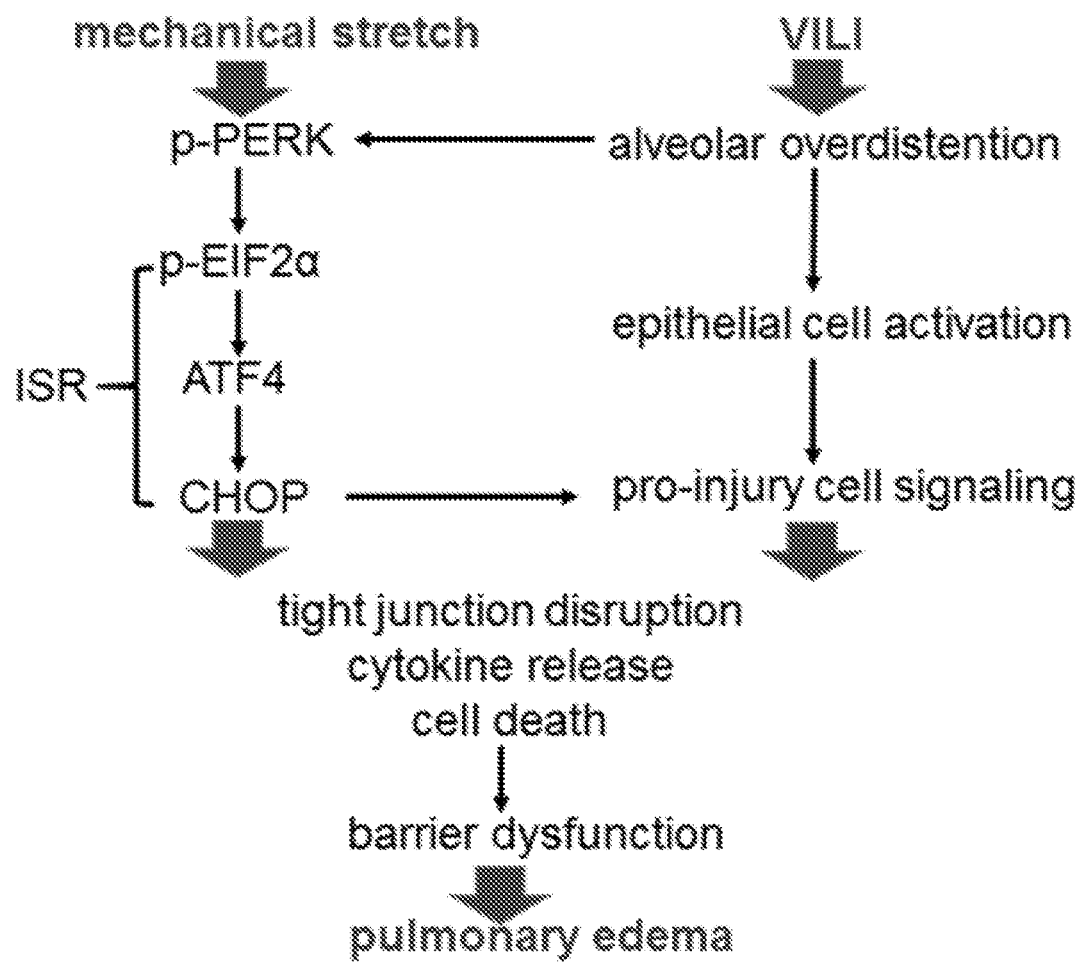
FIG. 15 illustrates the hypothetical role of ISR in the molecular pathology VILI. ISR=integrated stress response, PERK=protein kinase RNA-like endoplasmic reticulum kinase, EIF2α=eukaryotic initiation factor 2α, ATF4=activating transcription factor 4, CHOP=CCAAT/enhancer-binding protein homologous protein.

PI treatment did not result in immunosuppression in spontaneously breathing animals. In addition, VILI-induced pulmonary edema formation observed in vehicle-treated rats was significantly reduced in the PI-treated condition as measured with the surrogate parameter of increased BAL total protein content (FIG. 6E). PI pre-treatment significantly reduced alveolo-capillary permeability in the treatment group when compared to vehicle-treated animals (FIG. 6E). These findings were confirmed with FITC-labeled albumin extravasation index, a more sensitive and specific measurement of membrane integrity (FIG. 6F). Lung tissue-based analysis also showed decreased injury with PI treatment (FIG. 6G and FIG. 14). To evaluate pro-inflammatory cytokine release, IL-18 was measured. Mechanical ventilation increased IL-18 levels in BAL (FIG. 6H) and serum (FIG. 6I). A significant decrease of IL-18 in BAL was detected but not in serum of PI-treated animals. These results show that PI inhibition mitigates VILI. Furthermore, combined in vivo and in vitro data provides evidence that ISR regulates both alveolar permeability and pro-inflammatory signaling in the lung. Based on these experiment the overarching hypothesis, illustrated in FIG. 15, is that mechanical ventilation-induced overstretch of the alveolar epithelium and the lung tissue results in PERK autophosphorylation and subsequent phosphorylation of EIF2α. Concomitantly, p-EIF2α activates transcription factors ATF4 and CHOP downstream, resulting in pro-injury signaling. ISR-mediated injury signals induce early epithelial permeability changes, pro-inflammatory cytokine release and cell death, all contributing to barrier dysfunction and concomitant pulmonary edema formation.

Establishment of the Dose Response of PERK Pathway Inhibition in a Rat Model of VILI Groups of animals (Sprague-Drawly rats, 250 to 300 g weight purchased from Charles River Laboratories, N=150)) were pretreated with one time dose of 3, 10 and 30 mg/kg of PI (GSK2606414) or its vehicle (0.1% TWEEN 80 in 0.5% hydroxyethyl-methylcellulose) via oral gavage 4 hours before the start of the experiment. Subsequently, animals were randomized in the following conditions:

1. Non-ventilated controls pretreated with drug vehicle (C/VC). These animals were sacrificed 8 hours post gavage.
2. Low tidal volume ventilation group pretreated with vehicle (LTV/VC). These animals were anesthetized 4 hours post gavage and ventilated via tracheostomy for 4 hours with 6 ml/kg tidal volume, 3-5 cmH2O PEEP and lungs were recruited with 30 cmH2O pressure of air hourly. Animals were sacrificed at the end of 4 hours ventilation. This group will served as a second control to assess lung injury parameters in an optimized ICU care situation.
3. High tidal volume ventilation group pretreated with vehicle (HTV/VC). Animals were ventilated with 20 ml/kg tidal volume without PEEP or recruitment maneuver to induce lung injury and sacrificed at the end of mechanical ventilation period.
4. Controls with PI treatment (C/PI). Animals were sacrificed after 8 hours of PI treatment.

5. High tidal volume mechanical ventilation with PI treatment (HTV/PI). Animals were sacrificed at the end of mechanical ventilation period.

At the end of the experiment, lung tissue, BAL and serum was collected from all animals. To determine the optimal dose of PI in VILI, the following parameters were measured: BAL total protein measurement (BioRad Protein Assay, BioRad, Hercules, Calif.); lung tissue histology with hematoxylin-eosin (H&E) staining for lung injury scoring; BAL total and differential cell count; Serum and BAL cytokine analysis for IL-18 (R&D Systems, Minneapolis, Minn., USA); lung tissue was collected for future RNA and protein expression studies; blood pressure and heart rate recording (Coda Monitor, Kent Scientific, Torrington, Conn.); and/or animal mortality prior to the end of the experiment.

FIG. 21A-FIG. 21G depict that injurious mechanical ventilation increased indices of lung injury. Pretreatment with increasing doses of PI mitigated VILI and suggest that 10 mg/kg PI is sufficient to inhibit VILI.

In Vivo Validation of PERK Pathway Inhibition as a Therapeutic Modality in VILI

The detailed alveolar responses to PI treatment will be analyzed in this experiment. Animals will be randomized in the same experimental conditions above.

A) Permeability studies (N=5 animals/condition, total N=25). To study barrier function the extravasation of FITC-labeled albumin will be measured based on experiments by Chen H, Wu S, Lu R, Zhang Y G, Zheng Y, Sun J. Pulmonary permeability assessed by fluorescent-labeled dextran instilled intranasally into mice with LPS-induced acute lung injury. PLoS One. 2014; 9(7):e101925. This method is a more sensitive measurement of barrier function than BAL protein content or wet-to-dry lung weight ratio. FITC-labeled albumin (1 mg/animal) will be injected intravenously via the tail vein seven hours post gavage. Briefly, at the end of the experiment, BAL and serum will be collected and fluorescence will be measured at 488 nm wave lengths. Data will be expressed as fluorescent intensity (FI) ratio between BAL and serum. This experiment is partially completed (FIG. 21C) and its results suggest that increasing PI treatment dose has a gradual effect on reducing alveolocapillary permeability in VILI.

B) Static compliance measurement (N=5 animals/ventilation condition, total N=20). Changes in static lung compliance will be calculated for animals using a pressure transducer. Data will be expressed as the difference of compliance between measurements at the beginning and at the end of the mechanical ventilation period.

C) Epithelial co-immunofluorescence (IF) studies (N=5 animals/condition, total N=25). The direct effect of PI treatment on the alveolar epithelium will be studied with the stain intensity of p-EIF2α (Cell Signaling, Danvers, Mass.) localized to the epithelium. Epithelial localization will be detected with co-staining for AEC-I marker OCLN. The data will be expressed as relative density differences among the five experimental conditions.

The Mechanism of ISR-Mediated Epithelial Permeability

To investigate the mechanism of ISR on epithelial permeability, pretreated stretched monolayers were pretreated with PI and the expression of tight junction (TJ) proteins was compared to stretched and unstretched monolayers (FIG. 22). TJ proteins are critical in maintaining epithelial barrier function. Claudins (CLDN) and occludin (OCDN) are cell surface proteins that form junctions between epithelial cells and they are anchored to the cell by the intracellular protein zonula occludens-(ZO)-1. Claudin 4, 7 and 18 have been described in the epithelia as critical mediators of barrier function. Dissociation of CLDNs and OCLD from ZO-1 lead to barrier dysfunction and subsequently increased epithelial permeability. Using Co-immunoprecipitation assays for CLDN and OCLD with ZO-1 as bait, increased TJ dissociation was identified in response to stretch (FIG. 22A). Quantified immunoblotting analysis (FIG. 22B-FIG. 22E) shows that stretch impacts mainly on CLDN4 and 18 dissociation from ZO-1 and PI treatment prevents stretch-induced TJ dysfunction.

Vertebrate Animal Studies

Adult male Sprague-Dawley rats will be purchased from Charles River Laboratories (Horsham, Pa.). Rats will be allowed to acclimate for 1 week with rodent chow and water ad libitum. All animals will be housed in accordance with guidelines from the American Association for Laboratory Animal Care and Research protocols and approved by the Institutional Animal Care Use Committee at the University of Pennsylvania.

In Vitro Experiments (N=135)

Alveolar Epithelial Cell Isolation and AEC-I Monolayer Preparation and Stretch.

Rats (N=106) were euthanized with an overdose of sodium pentobarbital (55 mg/kg). The chest was shaved and cleaned with Wexcide. Tracheostomy was performed, and a 14 gauge (G) metal cannula was inserted in the trachea lumen. The animals were connected to a rodent ventilator (Harvard Apparatus Model 640, Holliston, Mass.). Subsequently, the chest and abdomen were opened by a midline incision, and the aorta was transected causing exsanguination. The apex of the heart was removed, and the pulmonary artery was catheterized via the right ventricle with a 14 G metal cannula and the lungs flushed with saline/glucose solution. Ventilation was stopped, and the lungs were perfused with a physiologic saline/glucose solution via the trachea cannula. The lungs were then removed en-bloc. The lung tissue was inflated with elastase (Worthington Biochemical Corporation, Lakeside, N.J.) and incubated at 37 C for 60 minutes. Lung tissue was then chopped to small pieces with scissors, and the tissue was filtered through a series of 450, 160 and 28 μm filters to obtain a single cell suspension. Next, epithelial cells were isolated using negative selection. The cells were plated on rat IgG coated plates containing serum-free media for 90 minutes at 37° C. to remove leukocytes and non-epithelial origin parenchymal cells. The remaining cells were collected. The isolation method yielded approximately 95% pure alveolar epithelial type-II (AEC-II) cells. Cells were plated on fibronectin-coated custom made silicone membranes. 1.3 million cells were plated on a 1 cm diameter membrane. Cells were cultured with 10% FBS-containing Minimal Essential Medium (MEM) containing antibiotics for 4 days to obtain monolayers. Rat AEC-II cells transformed to alveolar epithelial type-1 like (AEC-I) cells during this period of time and express only AEC-I cell surface markers. Over the course of 4 days they form a monolayer impermeable to large molecules. Typically, 40 to 70 million cells per rat were collected, which is sufficient to prepare 32 to 40 monolayers (1.3 million cells on a 1 cm diameter membrane). On the day of the experiment, the medium was removed and replaced with HEPES-buffered MEM. Cell stretch was performed in a 37° C. incubator. Monolayers were stretched (S) or used as unstretched controls (NS) in groups of 8 to obtain sufficient material for further analysis. Cells underwent biaxial 15/minute cyclic stretch with 25% surface change on our custom-built cell stretcher for 1 to 12 hours. For permeability studies, silasitc membranes were pre-treated with $O_2$ plasma to ensure even binding of fibronectin. Fibronectin was pre-mixed with 10 mM EZ-link biotin (Thermo Fisher Scientific, Waltham, Mass.) prior to cell plating. At the end of the experiment, cells were harvested by scraping for protein or RNA isolation. In permeability and cell death experiments, monolayers were directly stained. N=8 monolayers/condition were used as technical replicates for protein studies and N=3 monolayers/condition as technical replicates for RNA isolation, paracellular permeability and cell death measurements.

Multibead Assay for Cell Culture Supernatant Analysis.

Culture media of stretched and unstretched AEC-I monolayers was collected at the end of the experiment. N=5 biological monolayer replicates were used per condition. 0.5 ml samples were concentrated to 30 µl using centrifugal filters (Amicon Ultra, EMD Millipore). Levels of 26 common cytokines and chemokines were measured with RECYTMAG-65K MILLIPLEX MAP Rat Cytokine Chemokine Magnetic Bead Panel multiplex bead assay (EMD Millipore Corp., Billerica, Mass.) in triplicates per the manufacturer's protocol. 25 µl samples were used. The following analytes were measured: epidermal growth factor (EGF), eotaxin, macrophage colony stimulating factor (C-CSF), interleukin (IL)-1α, 2,4,5,6,10,12 (p70), 13, 17A, 18; granulocyte-macrophage colony stimulating factor (GM-CSF), regulated on activation, normal T cell expressed and secreted (RANTES), vascular epidermal growth factor (VEGF), fractalkine, interferon-γ (INFγ), interferon-γ-inducible protein 10 (IP-10), leptin, tumor necrosis factor-α (TNF-α), keratinocyte chemoattractant (GRO/KC), macrophage inflammatory protein (MIP)-1α and 2, monocyte chemoattractant protein (MCP-1), and LPS-induced chemokine (LIX). Samples were read in triplicates and an averaged value was obtained.

In Vivo Experiments (N=220)

PERK Inhibitor Treatment and Mechanical Ventilation Protocol.

Rats (N=32) received PERK inhibitor GSK 2606414 (PI) or vehicle control (0.1% Tween 80+0.5% hydroxypropyl-methylcellulose (VC)) via oral gavage 4 hours before the start of mechanical ventilation in 2.5 ml volume bolus. Subsequently, animals were randomized to receive mechanical ventilation, or they were let to breathe spontaneously (N=8/group). For the mechanical ventilation protocol, rats were kept under general anesthesia for the entire procedure. Their breathing, cardiac function and neurological responses were continuously monitored to minimize pain and distress. Induction and maintenance anesthesia was performed with inhaled 2-4% isoflurane. If additional anesthesia was necessary to keep the animal in surgical plane at the time of induction, it was given an intraperitoneal injection of a mixture of ketamine (75-100 mg/kg) and xylazine (5-10 mg/kg). To minimize injectable anesthesia and improve analgesia use, the subcutaneous tissue of the tracheostomy site was injected with 1% lidocaine. To ensure an adequate level of anesthesia, animals were continuously monitored for heart rate and blood pressure with the CODA noninvasive blood pressure tail cuff (Kent Scientific, Torrington, Conn.), and consciousness was monitored with a toe pinch every 15 minutes. A heat blanket was used to maintain ambient temperature of 38° C. throughout the experiment. Subsequently, the rats were tracheotomized; a 14-gauge metal cannula was placed in their trachea and sutured tight. Animals were mechanically ventilated for 4 hours with 20 ml/kg tidal volume with an Inspira advanced safety rodent ventilator (Harvard Apparatus, Holliston, Mass.). No positive end expiratory pressure (PEEP) was added, and no recruitment maneuvers were performed to maximize injury. At the end of the experiment, euthanasia was performed by thoracotomy and transection of great vessels.

Mechanical Ventilation Protocol.

Anesthetized animals will be tracheotomized, a 14 G metal cannula will be inserted in the trachea and suture in place. Animals will be connected to a Harvard Apparatus mechanical ventilator (Model 640) and ventilated with the tidal volume of 6 ml/kg (Low Tidal Volume, LTV) or 20 ml/kg (High Tidal Volume, HTV) for 4 hours. No positive end expiratory pressure (PEEP) will be added and no recruitment maneuvers will be performed for HTV condition to maximize injury. The LTV protocol will include PEEP=3-5 cmH2O and recruitment maneuvers every 60 minutes with 30 ml/kg.

Oral Gavage.

A 14 G curved needle will be used for gavage. Rats will receive of PERK inhibitor GSK 2606414 (PI) or vehicle control 0.1% Tween 80+0.5% hydroxypropyl-methylcellulose (VC) via oral gavage 4 hours before the start of mechanical ventilation in 2.5 ml volume bolus.

Necropsy and Tissue Harvest.

Following euthanasia, the chest cavity was opened with a midline incision. The right main stem bronchus was isolated, and a suture was placed around the bronchus. The left lung was lavaged with 3 ml cold PBS. The right lung was harvested. The right upper lobes were snap frozen and stored at −80° C. for protein and RNA extraction. The right lower lobe was perfused with 3% paraformaldehyde and used for histology. Total protein and RNA were extracted from lung tissue for western immunoblotting and gene expression studies. 1 ml blood from the left ventricle after euthanasia was collected. For cytokine analysis serum was used. Blood was left to coagulate for 2 hours at room temperature, and the serum was separated by centrifuging the samples at 5,000 RPM for 10 minutes in a tabletop centrifuge. Serum samples were stored at −80° C. for future analysis. 100 µl samples diluted to 1:2 was used to measure IL-18 cytokine expression with quantitative ELISA (# ELR-IL-18, RayBiotech, Norcross, Ga.). For permeability studies fresh plasma was obtained by collecting 1 ml blood in conical tubes containing 10 µl of 60 mg/ml EDTA.

RNA Extraction.

AEC-I were collected by scraping them in cell lysis buffer. RNA extraction was performed using the RNeasy protocol (Qiagen Sciences, Inc., Germantown, Md.). DNase digestion was performed. RNA yield was detected with a Nanodrop 8000 spectrophotometer (Thermo Fisher Scientific), and RNA fragment quality and size were analyzed using a Bioanalyzer 2100 (Agilent Technologies, Inc., Santa Clara, Calif.).

Bronchoalveolar Lavage (BAL) Sample Processing.

BAL samples were centrifuged at 5000 RPM for 10 minutes to separate cells from supernatant. The cell pellet was used for quantitative and qualitative cell counts. Cells were reconstituted in 1 ml PBS. Total BALF cell counts were obtained using a hemocytometer (Hausser Scientific, Horsham, Pa.). For differential cell count, 100 µl BALF was mounted on a glass slide by centrifuging the fluid at 1000 RPM for 10 minutes (Cytospin 2, Shandon Scientific, Runcorn, Cheshire, United Kingdom). Slides were stained with hematoxylin and eosin (H&E) and 200 cells were counted. Lavage supernatant was stored at −80° C. and later used for total protein measurement (Pierce BCA Protein Assay, Thermo Fisher Scientific) and quantitative ELISA cytokine analysis, as described above for serum samples.

Lung Tissue Histology and Immunofluorescence Analysis.

Paraformaldehyde fixed lung tissue was paraffin-embedded and consecutively sectioned. Tissue was used for H&E staining and immunofluorescence studies. For immunofluorescence staining, p-EIF2 (#3597, Cell Signaling Technology, Inc., Danvers, Mass.) and occludin (Invitrogen #33-1500, ThermoFisher Scientific) antibodies were used to stain formalin-fixed, paraffin-embedded tissue. Paraffin was cleared with xylene, and slides were rehydrated through descending concentrations of ethanol. Slides were then treated with 3% $H_2O_2$/methanol for 30 min. Slides were pretreated in a pressure cooker (Biocare Medical, LLC, Concord, Calif.) in Antigen Unmasking solution (H3300, Vector Laboratories, Burlingame, Calif.). After cooling, slides were blocked in Sudan Black (199664-25G, Sigma-Aldrich, St. Louis, Mo.) for 20 min at RT. Slides were then rinsed in 0.1M Tris Buffer, then blocked with 2% fetal bovine serum for 15 min. Slides were then incubated with pEIF2 antibody at a 1:200 dilution for 1 hr at room temperature. Slides were again rinsed, then incubated with anti-rabbit polymer secondary prediluted (K4003, DAKO, Carpenteria, Calif.) for 30 min at room temp. After rinsing, slides were then incubated with the TSA biotin complex (NEL7490B001, PerkinElmer, Waltham, Mass.) at 1:50 for 10 min at room temp. Slides were then rinsed and incubated with Alexa 488 Streptavidin (green) secondary (A21370, Life Technologies, Eugene, Oreg.) 1:200 for 30 min at room temp. After rinsing, slides were then treated in preheated 5% SDS (CS-5585-28, Denville Scientific, Metuchen, N.J.) for 7 min at 55° C. Slides were then rinsed and blocked with 2% fetal bovine serum again before incubating with occludin at 1:100 for 1 hour at room temp. After rinsing, slides were incubated for 1 hr in Alexa 594 a (red) anti-rabbit secondary (A11012, Life Technologies, Eugene, Oreg.). Slides were then rinsed, counterstained with DAPI, and rinsed again before cover slipping with Prolong Gold (P36930, Life Technologies, Eugene, Oreg.). Fluorescence was detected with Zeiss LSM 880 laser scanning confocal microscope using Plan Apo 20x objective with NA=0.8. Pictures were taken of 5 independent areas and green fluorescence was compared between control and ventilated lung tissue (N=3 animals/group). Fluorescent intensity was quantified using Fiji imaging software. Lung injury score was calculated as described by Matute-Bello and colleagues. In brief, scanned H&E slides (N=8/group) were enlarged to 100x magnification. Three independent 200 m by 200 m squares were selected on each slide. Scores were calculated based on the number of neutrophils in the alveolar space and the alveolar septi, the number of hyaline membranes, the amount of proteinaceous debris filling the airspaces and the alveolar wall thickness for each square. Score averages were provided for each slide. Three study staff blinded to the slide designation scored the tissue slides. Final scores were calculated as average of the 3 readings.

Serum Collection and Analysis.

One ml of whole blood will be obtained with cardiac puncture at the end of the experiment and collected in citrated vials. Plasma will be obtained by centrifuging the samples at 5000 RPM for 10 minutes. Plasma samples will be stored at −80° C. for further analysis. Plasma samples will be used to measure IL-18, IL-6 and MIP-1α with ELISA (reagents from, for example, R&D Systems)

Wet-to-Dry Lung Weight Ratio Measurement.

Lung tissue weight will be measured post-harvest and following 24h desiccation at 55° C. Weight ratio will be measured to evaluate lung edema formation.

Western Blotting and Immunoprecipitation for Protein Expression and Phosphorylation Studies.

Total protein from cells and lung tissue were extracted using RIPA lysis buffer. Total protein was quantified with Pierce BSA protein assay (Thermo Fisher Scientific). Western blotting for phosphorylated (p) and total (t) forms of EIF2α, p- and t-IRE1α, p- and t-PERK, ATF4, CHOP and XBP1 was performed. B-actin was used as loading control (Santa Cruz Biotechnologies, Santa Cruz, Calif.). The following primary antibodies were used: p-EIF2α (Ser 51) and t-EIF2α rabbit monoclonal antibody (Cell Signaling, Danvers, Mass.), p-IRE1α (Ser 724) and t-IRE1α rabbit monoclonal antibody (Abcam, Cambridge, Mass.), ATF4 rabbit polyclonal antibody (Sigma-Aldrich), CHOP (F-168) mouse polyclonal antibody (Santa Cruz), XBP-1 rabbit monoclonal antibody (Abcam) and B-actin mouse polyclonal antibody (Santa Cruz). For immunoprecipitation of PERK, p-PERK (Thr 981) antibody (Santa Cruz) was used and p-PERK (Thr 980) and t-PERK were detected with rabbit monoclonal antibodies (Cell signaling). N=4-8 biological replicates per conditions were used in immunoblot studies. Immunoblots were scanned and bend densities were analyzed using Image J software.

Endo/Epithelial Permeability Measurement with FITC-Labeled Albumin Extravasation.

The protocol described by Chen et al, *Pulmonary permeability assessed by fluorescent-labeled dextran instilled intranasally into mice with lps-induced acute lung injury*, PLoS One 2014; 9:e101925 was modified. In brief, animals (N=36, 9 animals/group) were injected with 1 mg/animal FITC-labeled bovine albumin (Sigma-Aldrich) diluted in 0.1 ml sterile saline 1 hour before sacrifice via the tail vein. Following sacrifice, undiluted bronchoalveolar lavage (BAL) and plasma were collected. The fluorescence of 100 μl of BAL and 1:10 diluted plasma was measured at 488 nm excitation and 520 nm emission wavelengths in duplicates (Cytofluor 4000 fluorescent plate reader, Perseptive Biosciences, Framingham, Mass.). The ratio of BAL to plasma fluorescence was used to express permeability.

Compliance Measurements.

Static compliance will be measured with a pressure transducer connected to the ventilator circuit (Harvard Apparatus, Holliston, Mass., USA) at the beginning and at the end of mechanical ventilation and data will be expressed as the difference between measurements.

siRNA Studies.

For siRNA studies, 3-day-old, almost matured monolayers were used. Monolayers were assigned to one of four conditions for 24 hours: 1) Transfection reagent treatment (OptiMem, Thermo Fisher Scientific) as the negative control for siRNA experiments, 2) Non-targeting siRNA treatment, as a negative control for transfection (On Target Plus non-targeting siRNA pool 1 and 2, Dharmacon Pharma, Pittsburgh, Pa.), 3) siRNA treatment to silence CHOP expression (On Target Plus Smart pool siRNA CHOP # L-088282 Dharmacon Pharma), siRNA treatment to silence ATF4 expression (On Target Plus Smart pool siRNA ATF4 #L-099212 Dharmacon Pharma), siRNA treatment to silence PERK expression (On Target Plus Smart pool siRNA PERK # L-044901 Dharmacon Pharma). N=4-5 biological monolayer replicates/condition were used, and monolayers were treated with 0.5 μg siRNA.

Sample Preparation for RNA Sequencing.

500 ng purified RNA per sample was used to generate libraries with Lexogen's QuantSeq 3'mRNA-Seq library prep kit from Illumina, FWD (Cat #015.24, Illumina, Inc., San Diego, Calif.). The QuantSeq kit generates one fragment per transcript and sequences obtained are close to the 3'end of polyadenylated RNA. Quality of purified libraries was checked using the High Sensitivity DNA kit for Bioanalyzer (Agilent Technologies, Inc.) and quantified using a KAPA library Quantification kit for Illumina platforms (Cat # KK4835, Kapa Biosystems, Inc., Wilmington, Mass.). Finally, equimolar concentrations of all libraries were pooled and subsequent sequencing of 75 bp single reads was performed on a NextSeq500 instrument using the NextSeq™ 500 Mid Output Kit (cat # FC-404-2001, Illumina, Inc.).

Quantitative RNA Sequencing (QuantSeq).

Quantitative mRNA sequencing was performed via QuantSeq. Sequencing libraries were obtained using the manufacturer's protocol (Lexogen, Vienna, Austria) on total RNA extracted from AEC-I cells. Sequencing was performed with an Illumina NextSeq 500 instrument (Illumina Inc., San Diego, Calif.) at the Wistar Institute (Philadelphia, Pa.). Reads for each sample were aligned with STAR (v.2.5.1b) to the reference *Rattus norvegicus* build 6 UCSC file (m6) genome obtained from the Illumina, Inc. iGenomes resource (9). For each sample, HTSeq (v.0.6.1) was used to quantify genes based on reads that mapped to the provided m6 reference files (10). The DESeq2 R package (v.1.10.1) was used to measure significance of differentially expressed genes between the stretched (N=5) and not-stretched (N=5) samples and create plots of the results (11). The reported adjusted p-values are false-discovery rate corrected to 5% according to the procedure in DESeq2 that accounts for the large number of comparisons made. An adjusted p-value <0.05 was considered significant. The NIH Database for Annotation, Visualization and Integrated Discovery (DAVID) was used to perform gene functional annotation clustering using *Rattus Norvegicus* as background, and default options and annotation categories (Disease: OMIM_DISEASE; Functional Categories: COG_ONTOLOGY, SP_PIR_KEYWORDS, UP_SEQ_FEATURE; Gene_Ontology: GOTERM_BP_FAT, GOTERM_CC_FAT, GOTERM MF_FAT; Pathway: BBID, BIOCARTA, KEGG_PATHWAY; Protein_Domains: INTERPRO, PIR_SUPERFAMILY, SMART).

RNA Analysis.

Global quantitative mRNA measures were obtained via QuantSeq (Lexogen, Vienna, Austria). Sequencing libraries were prepared from AEC-I total RNA. Reads were aligned with STAR (v.2.5.1b) to the reference *Rattus norvegicus* build6 and DESeq2 R package was used to measure significance of differentially expressed genes between the stretched and unstretched samples. The data is available in the Gene Expression Omnibus (GEO) under accession GSE89024. Il18 gene expression of PERK siRNA treated and control cells was performed with TaqMan PCR.

TaqMan Quantitative Real Time PCR.

TaqMan real time PCR was performed for Il18 on 500 ng total RNA extracted from AEC-I cells. Non-targeting or PERK specific siRNA treated cells were exposed to mechanical stretch (25% surface area change for 6 hours) and RNA expression was compared to unstretched cells. TaqMan RT-PCR was performed as described previously (Ning W, Chu T J, Li C J, Choi A M, Peters D G. Genome-wide analysis of the endothelial transcriptome under short-term chronic hypoxia. Physiol Genomics, 2004; 18:70-78.). Commercially available Assay-on-Demand primer probe sets (Applied Biosystems, ThermoFisher) were used for rat Il18 (Rn01422083_ml). Gene expression was measured relative to an endogenous reference gene, rat β-glucuronidase (Gusb, Rn00566655_ml). The results were log 2 base transformed and the arithmetical means of measurements were compared using Applied Biosystem's Data Assist software (version 3.01). N=4 biological replicates were analyzed for each condition and samples were run in triplicates.

Statistics.

For comparative studies of densitometry, cytokine levels, qPCR and cell count the Kruskal-Wallis test was used for multi-group comparisons and intergroup differences were analyzed with the Wilcoxon rank sum test. For fluorescent image intensity analysis, ANOVA testing test was used (JMP software, Cary, N.C.). Results are presented as mean±SEM. Significance level was P<0.05.

Fluorescent Imaging Analysis for Paracellular Permeability and Cell Death Measurements.

To measure permeability, the silastic membranes were coated with biotinylated fibronectin and cells were cultured on the apical surface. The monolayers were stained with FITC (Alexa Fluor 488)-labeled streptavidin (Thermo Fisher Scientific, Waltham, Mass.) 15 minutes before the end of the experiment. At the end of the experiment, unstretched and stretched monolayers were placed in a humidified incubator until further processing. Light emission at 488 nm was measured for monolayers using fluorescent microscopy (Nikon TE300, Melville, N.Y.). Under physiological conditions, the monolayer is impermeable to large molecules, which prevents streptavidin-biotin binding. Prolonged cyclic stretch results in cell-cell contact disruption and subsequent biding of streptavidin to the membrane-bound biotin. The emitted fluorescence is proportional to the monolayer damage caused by stretch and is detectable by fluorescent microscopy. Images of 3 independent areas of each monolayer were captured, and the intensity of light emission values were normalized to maximum pixel density of the background using custom designed software (Matlab, Mathworks, Natick, Mass.), described in Song M J, Davidovich N, Lawrence G G, Margulies S S. Superoxide mediates tight junction complex dissociation in cyclically stretched lung slices. *Journal of biomechanics* 2016; 49:1330-1335. The maximum pixel intensity in the background of unstretched-untreated monolayers was measured and used as a threshold to exclude unstained regions. The percentage of each image area above the threshold intensity was determined and then divided by the value for the unstretched control group to calculate the normalized area percentage (nArea) of each image. To test the effect of a stretch condition, n Area values were compared with control group values using a one-way ANOVA with post hoc Dunnett's test in JMP (SAS Institute, Cary, N.C.). To test the effect of inhibitor treatment, n Area values were compared with vehicle controls using a two-way ANOVA with Tukey-Kramer post hoc analysis in JMP. Data were expressed as ±SEM. To assess stretch-induced cell death, dead to live cell ratio was quantified with triple ethidium homodimer (dead cells)-Calcein-AM (live cells) and nuclear (DAPI) stain (Thermo Fisher Scientific). Fluorescent light emission for ethidium homodimer (excitation/emission wave length: 528/617 nm) and Calcein-AM (excitation/emission wave length: 494/517 nm) was captured with fluorescent microscopy (Nikon TE300). 100 cells were counted and the percentage of live and dead cells was calculated.

Data Interpretation

Increased PERK-mediated ISR signaling was observed in alveolar epithelial cells in response to cyclic stretch and mechanical ventilation. The alveolar epithelium showed ISR-dependent permeability increase, proinflammatory cytokine production and cell death. Inhibition of PERK signaling mitigated lung injury signals in vitro and in vivo. This novel observation provides the first evidence that ISR regulates alveolar epithelial homeostasis in response to mechanical stimuli. The presently disclosed examples also show that ISR activation is time-dependent and may affect cellular function, independent of cell death in the alveolar epithelium. In the absence of significant cell death, ISR transcription factor activation follows a bimodal pattern. With EIF2α phosphorylation, ATF4 initially responds with increased expression and subsequently upregulates CHOP transcription. With continued EIF2α activation, there is an adaptive transcription factor downregulation to prevent cell premature cell death. In the present model, ISR signal peaks at 6 hours, with an adaptive decrease in ATF4 and CHOP by 12 hours in the presence of persistent EIF2α activation. Increased epithelial barrier permeability was observed without significant cellular death following 6 hours of stretch exposure. This data suggests that early epithelial barrier dysfunction is caused by tight junction protein. It is also known that ISR interacts with $Ca^{2+}$ signaling and members of the Rho kinase family of small molecule guanylyltriphosphates, both critical modulators of tight junction integrity and alveolar epithelial cell permeability in cyclic stretch.

The UPR-responsive IRE1α and ATF6 pathways are described in the literature as parallel mechanisms to PERK-mediated ISR. They co-regulate protein synthesis in response to cellular stress and have overlapping function. Experiments with PERK-null mice suggest that IRE1α and ATF6 can compensate for the loss of PERK. However, the same mice develop an inflammatory phenotype with severe pancreas insufficiency, bone abnormalities and premature mortality demonstrating that the three pathways also have independent roles. This paradigm can be explained by the three pathways' different sensitivities to various forms of endoplasmic reticulum stress. The instant cell stretch model describes how PERK-mediated ISR activation is independent of the IRE1α pathway. These findings suggest that PERK is a specific sensor of mechanical stretch and that this effect is independent of UPR. Similarly, it has been previously shown that mouse fibroblasts respond to mechanical force tension with PERK-induced apoptosis without IRE1α or ATF6 signaling. The present in vitro findings are strengthened by the striking inhibition of inflammation and alveolocapillary permeability by PI in the rat VILI model. Based on these observations, it may be concluded that selective PERK inhibition can be used to manipulate cellular responses to stretch and thereby mitigate epithelial injury.

The comprehensive cytokine profiling resulted in the identification of MIP-1α, IL-1α and IL-18 as markers of epithelial injury. Only low levels of cytokines are released from the alveolar epithelium in response to physiological magnitude of cell stretch and they have not been shown to contribute to alveolar damage. However they may serve as mediators of injury signals. Epithelial-derived MIP-1α is a strong neutrophil chemoattractant which has been shown to induce IL-1 and TNF-α secretion from recruited inflammatory cells. IL-1α released from damaged epithelial cells resulted in fibroblast activation in a model of pulmonary fibrosis. It has been previously reported that the deletion of IL-18 from colonic epithelial cells cause increased gut permeability and severe colitis, and that IL-18 as a critical mediator of lung injury in patients with sepsis and ARDS. After further investigation of the control of released IL-18 from the epithelium it was found that it is equally regulated by PERK, ATF4 and CHOP post transcription. In macrophages, which are the major source of the cytokine, IL-18 is produced in its pro-form by the nucleotide-binding oligomerization domain (NOD)-like receptor (NLR)-containing inflammasomes and cleaved to its active (matured) form by Caspase (CASP)-1. The NLRP3 inflammasome which is most studied in response to pro-inflammatory signals is sensitive to CHOP activation. In lung parenchymal cells, Il18 mRNA is constitutively expressed and RNA levels reflect pro-IL 18 protein levels. The instant data sheds light to a new mechanism via IL-18 is controlled in the epithelium and more importantly strengthens the hypothesis that epithelial cytokine levels are modulated upon stretch response. While the direct benefit of reduced IL-18 levels on alveolar permeability was not investigated, the combined in vitro and in vivo data suggests that IL-18 should be investigated further as a marker of alveolar injury.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

The disclosures of each patent, patent application, and publication cited or described in this document are hereby incorporated herein by reference, in its entirety.

EMBODIMENTS

The following list of embodiments is intended to complement, rather than displace or supersede, the previous descriptions.

Embodiment 1

A method of treating lung injury and/or lung inflammation in a subject comprising administering to the subject a therapeutically effective dose of a PERK pathway inhibitor to prevent and/or treat the lung injury and/or inflammation.

Embodiment 2

The method of embodiment 1, wherein the lung injury comprises acute respiratory distress syndrome or ventilator-induced lung injury.

Embodiment 3

The method of embodiment 1 or 2, wherein the PERK pathway inhibitor comprises a small molecule or siRNA.

Embodiment 4

The method of embodiment 3, wherein the siRNA inhibits expression of a nucleic acid encoding CHOP, ATF-4 or PERK.

Embodiment 5

The method of embodiment 3, wherein the small molecule comprises a PERK inhibitor.

Embodiment 6

The method of embodiment 5, wherein the PERK inhibitor is 1-[5-(4-Amino-7-methyl-7H-pyrrolo[2,3-d]pyrimidin-5-yl)indolin-1-yl]-2-(3-trifluoromethylphenyl)ethanone.

Embodiment 7

A method of preventing lung injury and/or lung inflammation in a subject comprising administering to the subject a therapeutically effective dose of a PERK pathway inhibitor to prevent and/or treat the lung injury and/or inflammation.

Embodiment 8

The method of embodiment 7, wherein the lung injury comprises acute respiratory distress syndrome or ventilator-induced lung injury.

Embodiment 9

The method of embodiment 7 or 8, wherein the PERK pathway inhibitor comprises a small molecule or siRNA.

Embodiment 10

The method of embodiment 9, wherein the siRNA inhibits expression of a nucleic acid encoding CHOP, ATF-4 or PERK.

Embodiment 11

The method of embodiment 9, wherein the small molecule comprises a PERK inhibitor.

Embodiment 12

The method of embodiment 11, wherein the PERK inhibitor is 1-[5-(4-Amino-7-methyl-7H-pyrrolo[2,3-d]pyrimidin-5-yl)indolin-1-yl]-2-(3-trifluoromethylphenyl)ethanone.

Embodiment 13

A pharmaceutical composition for the prevention and/or treatment of lung injury and/or lung inflammation comprising PERK pathway inhibitor.

Embodiment 14

The pharmaceutical composition of embodiment 13, wherein the lung injury comprises acute respiratory distress syndrome or ventilator-induced lung injury.

Embodiment 15

The pharmaceutical composition of embodiment 13 or 14, wherein the PERK pathway inhibitor comprises a small molecule or siRNA.

Embodiment 16

The pharmaceutical composition of embodiment 15, wherein the siRNA inhibits expression of a nucleic acid encoding CHOP, ATF-4 or PERK.

Embodiment 17

The pharmaceutical composition of embodiment 15, wherein the small molecule comprises a PERK inhibitor.

Embodiment 18

The pharmaceutical composition of embodiment 17, wherein the PERK inhibitor is 1-[5-(4-Amino-7-methyl-7H-pyrrolo[2,3-d]pyrimidin-5-yl)indolin-1-yl]-2-(3-trifluoromethylphenyl)ethanone.

Embodiment 19

Use of a PERK inhibitor in the manufacture of a medicament for the prevention or treatment of a lung injury and/or lung inflammation.

Embodiment 20

The use of embodiment 19, wherein the PERK inhibitor is 1-[5-(4-Amino-7-methyl-7H-pyrrolo[2,3-d]pyrimidin-5-yl)indolin-1-yl]-2-(3-trifluoromethylphenyl)ethanone.

Embodiment 21

A PERK inhibitor for use in the prevention and/or treatment of lung injury and/or lung inflammation.

Embodiment 22

The PERK inhibitor of embodiment 21, wherein the PERK inhibitor is 1-[5-(4-Amino-7-methyl-7H-pyrrolo[2,3-d]pyrimidin-5-yl)indolin-1-yl]-2-(3-trifluoromethylphenyl)ethanone.

What is claimed is:

1. A method of treating lung injury and/or lung inflammation in a subject comprising administering to the subject a therapeutically effective dose of a PERK inhibitor to treat the lung injury and/or inflammation, wherein the PERK inhibitor is 1-[5-(4-Amino-7-methyl-7H-pyrrolo[2,3-d]pyrimidin-5-yl)indolin-1-yl]-2-(3-trifluoromethylphenyl)ethanone.

2. A method of preventing lung injury and/or lung inflammation in a subject comprising administering to the subject a therapeutically effective dose of a PERK inhibitor to prevent the lung injury and/or inflammation, wherein the PERK inhibitor is 1-[5-(4-Amino-7-methyl-7H-pyrrolo[2,3-d]pyrimidin-5-yl)indolin-1-yl]-2-(3-trifluoromethylphenyl)ethanone.

3. The method of claim 1, wherein the lung injury comprises acute respiratory distress syndrome.

4. The method of claim 1, wherein the lung injury comprises ventilator-induced lung injury.

5. The method of claim 2, wherein the lung injury comprises acute respiratory distress syndrome.

6. The method of claim 2, wherein the lung injury comprises ventilator-induced lung injury.

* * * * *

UNITED STATES PATENT AND TRADEMARK OFFICE
CERTIFICATE OF CORRECTION

PATENT NO. : 11,026,945 B2
APPLICATION NO. : 16/096721
DATED : June 8, 2021
INVENTOR(S) : Margulies et al.

It is certified that error appears in the above-identified patent and that said Letters Patent is hereby corrected as shown below:

In the Specification

Under Column 4, Line no. 17, Replace:
"S+ PI, t-test"
With:
-- S+PI, t-test. --

Under Column 13, Line no. 24, Replace:
"treatment can mitigate stretch-induced epithelial damage"
With:
-- treatment can mitigate stretch-induced epithelial damage. --

Under Column 13, Line no. 47, Replace:
"posttranscriptional modification of IL-18 in the alveolar epithelium"
With:
-- posttranscriptional modification of IL-18 in the alveolar epithelium. --

Under Column 16, Line no. 4, Replace:
"expressed as mean and standard error of mean (±SEM)"
With:
-- expressed as mean and standard error of mean (±SEM). --

Under Column 23, Line no. 67, Replace:
"(reagents from, for example, R&D Systems)"
With:
-- (reagents from, for example, R&D Systems). --

Signed and Sealed this
Third Day of August, 2021

Drew Hirshfeld
*Performing the Functions and Duties of the*
*Under Secretary of Commerce for Intellectual Property and*
*Director of the United States Patent and Trademark Office*